(12) United States Patent
Matsui et al.

(10) Patent No.: US 7,824,886 B2
(45) Date of Patent: Nov. 2, 2010

(54) DNA REPLICATION FACTORS

(75) Inventors: Ikuo Matsui, Tsukuba (JP); Yuji Urushibata, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 493 days.

(21) Appl. No.: 11/748,961

(22) Filed: May 15, 2007

(65) Prior Publication Data

US 2007/0264660 A1    Nov. 15, 2007

(30) Foreign Application Priority Data

May 15, 2006    (JP)    ............................. 2006-135634

(51) Int. Cl.
*C12P 19/34*    (2006.01)
*A61K 38/16*    (2006.01)

(52) U.S. Cl. ...................... 435/91.1; 435/194; 530/350; 530/358

(58) Field of Classification Search ....................... None
See application file for complete search history.

(56) References Cited

U.S. PATENT DOCUMENTS 7,442,766 B2 *  10/2008  Hogrefe et al. .............. 530/350

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner*—Richard G Hutson
(74) *Attorney, Agent, or Firm*—Oblon, Spivak, McClelland, Maier & Neustadt, L.L.P.

(57) ABSTRACT

A DNA polymerase reaction system which provides high DNA polymerase activity even at a high temperature and at a high salt concentration. A DNA polymerase reaction system that is constructed from a DNA polymerase, a clamp, and a clamp loader without intein sequence, the DNA polymerase being from *Pyrococcus horikoshii*, a hyperthermophilic archaeon.

10 Claims, 14 Drawing Sheets

Fig. 1

```
gtggtgctgatggagcttccaaaggaaatggaagagtacttttccatgttacagagggag
atagataaagcttatgagatagccaagaaggctagagctcagggtaaggatcctagcttg
gatgttgagatccctcaagcttctgacatggccggaagagttgaaagcttagtcggcccc
ccaggagttgccgaaagaattagggagctagttaaggaatatggtaaggagatagctgct
ctcaaaatagttgatgagataatagatggaaaattcggtgatctggggaagtaaggaaaag
tatgctgaacaggccgtaaggacggcccttgccatactaactgaaggtgtagtttccgct
ccaattgagggaatagctagtgttaagataaagaggaacacatggtccgataattctgag
tatttagctctctactatgctgggccaatcagaagctctggaggaacggcccaagcgcta
agtgttctcgttggcgactacgtgaggagaaagctaggccttgatagatttaagccaagt
gaaaagcacatagaaagaatggttgaggaagttgatctctatcataggactgtttctaga
ctacagtatcatccttccccagaggaagtaaggttagctatgaggaatattccaattgaa
attactggagaagctacggatgaagttgaagtttctcacagagatatccctggagtggaa
accaaccaacttaggggtggtgctattctagtcctagcggagggagttcttcagaaggcc
aagaagttagttaaatatatagataagatgggaattgaaggttgggagtggcttaaagaa
ttcgtcgaagctaaggaaaagggagaagaaattgaagaggaaggatctgctgaatcaaca
gttgaagagacaaaggtagaagttgacatgggcttttactactctctctatcagaagttc
aaatctgagattgctccaaatgataagtatgctaaggaaataataggtgggagacctctc
ttctcagatccctccaggaatggaggatttaggctacgctatggaaggagcagggtgagt
ggatttgcaacttggggaataaatccagcgacaatgattttagttgatgagttcttagcc
attgggactcaattaaagactgagagaccaggaaagggcgctgtggtaactcctgtaact
actatagagggcccaatagtcaagctcaaggatggtagcgtagtgaaggttgacgattac
aagctagccctcaagatcagggatgaagttgaggagatcttatacttaggggatgctgtc
attgcttttggtgacttcgttgagaataatcagaccctccttccggccaattattgcgaa
gagtggtggatactggaatttacgaaggctctcaatgaaatttatgaagtggagcttaaa
ccatttgaagttaattcgagtgaagatcttgaggaagcggcagattatctcgaggttgac
attgaattttgaaagagctacttaaggatcccttaaggactaagcctccagttgagctt
gctattcatttctccgaaatacttgggataccccttcatccgtattataccctctattgg
aattccgtgaagcccgagcaagtggagaagctttggagggtgctcaaggaacacgctcat
atcgactgggataacttcaggggaattaagtttgccaggaggatagttataccoctagaa
aaacttagagattctaagagagcccttgagctcctgggacttccacataaggtggagggt
aaaaacgttatcgttgattatccctgggctgcagctctattaactccccttggcaatctt
gagtgggagttcagagctaaaccttacacacgaccatagatatcataaacgaaaacaat
gagattaagcttagggatagggaataagctggatagggccaggatggggaggcccgag
aaagctaaggagagaaagatgaagcctcctgttcaagttctcttcccaataggacttgct
ggtggaagtagtagagatataaagaaggccgctgaggagggtaaggttgccgaggttgaa
atagccctcttcaagtgccccaaatgtggtcacgttggccctgagcatatctgtcccaac
```

Fig. 1 (continued)

tgtggaaccaggaaggaattgatctgggtatgccctaggtgtaacgcggagtaccccgag
agccaggcaagtggctataactacacctgtccaaagtgcaacgttaagctaaagccttat
gctaagagaaagataaagccatcagagttgcttaagagggccatggataatgtcaaagtt
tatggcattgacaagctgaagggagttatgggaatgacatccggctggaaaatgccggaa
cctctggagaaaggacttcttagggctaaaaatgatgtatatgtgtttaaagatgggaca
attaggtttgacgccactgatgctccaataacccatttagacccagagaaattggagtt
tcagttgagaaacttagagagctgggtatacccacgacttcgagggtaatcccttggtt
agcgaagatcagatagttgagcttaagcctcaggatattatactctccaaagaagcaggt
aaatacctttgaaagttgcaaagttcgttgatgacctccttgagaagttttatggtctt
ccaaggttctacaatgctgagaagatggaagatctaattggacatttggtgatagggctt
gctcctcacacttccgctggaatcgtcggaaggatcatagggttcgttgatgccttggtt
ggttatgctcatccctacttccacgctgcaaagaggagaaattgcttcccgggagataca
agaatattagttcaaattaatggaactccgcagagagttacacttaaggaattatatgag
ctctttgacgaggaacattatgaaagcatggtgtacgtaaggaaaaagccaaaggtagac
attaaggtatactccttcaaccctgaggaaggtaaggtagttctgaccgatattgaggag
gtaataaaagcccctgctactgatcatttaattcgctttgaacttgagctcggaagtagc
tttgagacaaccgtggatcacccagtcctcgtatatgaaaatggaaagttcgtgagaaa
agggcatttgaggttagggaggggaatataataattataatcgatgaatcaactttggaa
ccccttaaggttgctgttaaaaaaatagagttcatagaaccgcctgaggactttgtgttc
tctcttaatgctaaaaaatatcatactgtaataattaatgaaaatattgtgacgcatcag
tgccgatggtgatgaagatgctgtcatgttgctcctggatgctttactaaacttttcccgc
tattatcttccagagaagcgtggtggaaagatggatgccccattggtcatcacaacgcgc
ttagatccgagggaagttgatagcgaggttcataacatggatatagtcaggtactatcct
ctcgagttttatgaggctacctacgaacttaagtctccaaaggagttggtaggagttatt
gagagagtcgaggatagattgggaaaacctgaaatgtattatgggctgaagttcacccac
gacacggatgatatagccctcggccctaagatgagcctttacaagcaattgggagatatg
gaagaaaaagtgaagaggcaacttgacgtcgccaggaggatcagggccgttgatgagcat
aaagttgctgagacgatactcaattctcatttgatccctgatcttagggtaatttgaga
agctttactaggcaggagttccgttgtgtgaagtgcaacacaaagtttaggagacctccc
ctcgatggtaaatgtccaatttgcggaggaaaaatagtgctcaccgttagtaaaggggcc
atagagaagtatcttgggacggctaagatgctggtgacggagtacaaagttaaaaactat
acgaggcagaggatatgcttaaccgagagggatatagattccctgtttgaaactgtattt
ccggagactcagttaacgcttctcgttaatcccaatgacatatgtcagagaattatcatg
gaaaggactggaggggagcaaaaaatcgggcctcctagaaaactttgctaacggttataat
aaggggaagaagaagaaatgcctaaaaagcaaagaaagaaggagcaggaaaagtcaaag
aaaagaaaagtaattagcctagatgatttcttctcaaggaaataa

Fig. 2

MVLMELPKEMEEYFSMLQREIDKAYEIAKKARAQGKDPSLDVEIPQASDMAGRVESLVGP
PGVAERIRELVKEYGKEIAALKIVDEIIDGKFGDLGSKEKYAEQAVRTALAILTEGVVSA
PIEGIASVKIKRNTWSDNSEYLALYYAGPIRSSGGTAQALSVLVGDYVRRKLGLDRFKPS
EKHIERMVEEVDLYHRTVSRLQYHPSPEEVRLAMRNIPIEITGEATDEVEVSHRDIPGVE
TNQLRGGAILVLAEGVLQKAKKLVKYIDKMGIEGWEWLKEFVEAKEKGEEIEEEGSAEST
VEETKVEVDMGFYYSLYQKFKSEIAPNDKYAKEIIGGRPLFSDPSRNGGFRLRYGRSRVS
GFATWGINPATMILVDEFLAIGTQLKTERPGKGAVVTPVTTIEGPIVKLKDGSVVKVDDY
KLALKIRDEVEEILYLGDAVIAFGDFVENNQTLLPANYCEEWWILEFTKALNEIYEVELK
PFEVNSSEDLEEAADYLEVDIEFLKELLKDPLRTKPPVELAIHFSEILGIPLHPYYTLYW
NSVKPEQVEKLWRVLKEHAHIDWDNFRGIKFARRIVIPLEKLRDSKRALELLGLPHKVEG
KNVIVDYPWAAALLTPLGNLEWEFRAKPLHTTIDIINENNEIKLRDRGISWIGARMGRPE
KAKERKMKPPVQVLFPIGLAGGSSRDIKKAAEEGKVAEVEIALFKCPKCGHVGPEHICPN
CGTRKELIWVCPRCNAEYPESQASGYNYTCPKCNVKLKPYAKRKIKPSELLKRAMDNVKV
YGIDKLKGVMGMTSGWKMPEPLEKGLLRAKNDVYVFKDGTIRFDATDAPITHFRPREIGV
SVEKLRELGYTHDFEGNPLVSEDQIVELKPQDIILSKEAGKYLLKVAKFVDDLLEKFYGL
PRFYNAEKMEDLIGHLVIGLAPHTSAGIVGRIIGFVDALVGYAHPYFHAAKRRN<u>CFPGDT
RILVQINGTPQRVTLKELYELFDEEHYESMVYVRKKPKVDIKVYSFNPEEGKVVLTDIEE
VIKAPATDHLIRFELELGSSFETTVDHPVLVYENGKFVEKRAFEVREGNIIIIDESTLE
PLKVAVKKIEFIEPPEDFVFSLNAKKYHTVIINENIVTHQCDGDEDAVMLLLDALLNFSR</u>
YYLPEKRGGKMDAPLVITTRLDPREVDSEVHNMDIVRYYPLEFYEATYELKSPKELVGVI
ERVEDRLGKPEMYYGLKFTHDTDDIALGPKMSLYKQLGDMEEKVKRQLDVARRIRAVDEH
KVAETILNSHLIPDLRGNLRSFTRQEFRCVKCNTKFRRPPLDGKCPICGGKIVLTVSKGA
IEKYLGTAKMLVTEYKVKNYTRQRICLTERDIDSLFETVFPETQLTLLVNPNDICQRIIM
ERTGGSKKSGLLENFANGYNKGKKEEMPKKQRKKEQEKSKKRKVISLDDFFSRK

Fig. 3

```
gtgcataatatggaagaggttagagaggtaaaggttcttgaaaaaccatgggttgaaaag
tataggcctcagagattagatgagatagtgggtcaagagcatatagttaagaggcttaaa
cactacgttaaaactgggtcaatgccccatttactatttgcaggtcctcctggtgttgga
aagtgcctcaccggagatactaaagttatagctaacggtcaactcttcgaacttagggag
cttgtcgaaaaaatctccggaggaaaattcggcccaactcccgttaaggggttaaaagtt
attgggatagatgaagatggaaagcttagagagttcgaagttcaatatgtttacaaagat
aaaactgagaggctaataaggataaggactcgccttggaagggagcttaaggtaacccca
taccatcccctcctcgtgaatagaaggaacggagagataaagtgggttaaagccgaagaa
ctcaaacctggtgacaaacttgcggtaccgcgtttcttacccattgtaaccggagaagat
cctctggcagagtggcttggctacttcctcggaggcggttatgctgactcaaaggagaac
ttaatcatgtttaccaatgaagatcccctcctaagacaacgcttcatggagctaacggaa
aagcttttctcagatgcaaggataagggagataacccacgagaatggaacttcaaaagtt
tatgtaaactccaagaaagccttaaagctagtaaactccctaggaaatgctcacataccc
aaagaatgctggagaggaattcggtctttcctcagggcttacttcgactgcaatggtggc
gtcaaggggaacgctatagtcctagcaacagctagcaaggagatgtcccaggaaatagca
tatgctctagccggcttttggaataatctcaaggatacaagaataccgcgttattatatca
ggctcagataacgtaaagaagttcctaaatgagatcggctttattaatcggaataaactt
gaaaaggccctaaagcttgttaaaaaagatgatccaggtcatgatggcttggagatcaac
tatgagctaatatcctacgttaaagataggcttaggttaagtttctttaacgataagaga
agttggagctacagagaagcgaaggaaatttcctgggagctgatgaaagagatctactac
cgccttgatgagcttgagaagctgaaagagtctttgtcaaggggtatcctaatcgactgg
aacgaagtagcaaagaggatagaagaggtagcagaagaaactggaattagagcagatgaa
ctccttgagtacatagaaggaaaaagaaagctgagtttcaaggattacataaagatagca
aaggttcttggaattgacgttgaacataccatcgaagctatgagagttttttgcaagaaag
tattcaagctacgctgagattggaaggagactcggtacctggaattctagcgtgaagaca
attctcgagagcaacgccgtgaacgttgaaatcctagagaggataaggaaaattgaactt
gaactcatagaggaaatactctccgatgaaaagctcaaggaagggatagcgtacttaatc
ttcctctcgcaaaatgagctttattgggatgagataactaaagtagaagagcttagggga
gagttcataatctacgatcttcacgttcctgggtaccacaacttcatagctggaaacatg
ccaacggtagttcacaatactacagcagctttagccctctcaagagagcttttcggcgag
aactggaggcataatttccttgaattgaatgcttcagatgagagaggtataaacgtgatt
agagagaaagttaaggagtttgcaaggacaaaacccataggaggagcgagcttcaagata
atcttccttgacgaggccgacgctttaactcaagatgcccagcaagcattaaggagaacc
atggagatgttctcgagcaacgttcgctttatcttaagctgtaactactcctcaaagatc
attgagcccatacagtctagatgtgcgatattccgcttcagacccctccgtgatgaggac
atagcaaagagattaaggtacattgccgaaaatgaaggtttagagctaactgaagaaggt
ctccaagcaatactttacatagccgaaggagacatgagaagggccataaacattctgcaa
gctgcagcggccctggacaagaaaattaccgatgaaaatgtattcatggtagcgagtagg
gctagaccagaggatataagggagatgatgctcttagcccttaagggtaacttcctgaag
gctagagaaaagctcagggaaatactcctcaagcaggggcttagtggagaggatgtctta
attcagatgcacaaagaggtatttaacttaccgatagatgagcccactaaagtttaccta
gcggataagataggagagtacaacttcaggctcgttgaaggagctaacgagatgatacag
cttgaagccctcttagctcaatttaccttagttggaaagaagaagtga
```

Fig. 4

MHNMEEVREVKVLEKPWVEKYRPQRLDEIVGQEHIVKRLKHYVKTGSMPHLLFAGPPGVG
KCLTGDTKVIANGQLFELRELVEKISGGKFGPTPVKGLKVIGIDEDGKLREFEVQYVYKD
KTERLIRIRTRLGRELKVTPYHPLLVNRRNGEIKWVKAEELKPGDKLAVPRFLPIVTGED
PLAEWLGYFLGGGYADSKENLIMFTNEDPLLRQRFMELTEKLFSDARIREITHENGTSKV
YVNSKKALKLVNSLGNAHIPKECWRGIRSFLRAYFDCNGGVKGNAIVLATASKEMSQEIA
YALAGFGIISRIQEYRVIISGSDNVKKFLNEIGFINRNKLEKALKLVKKDDPGHDGLEIN
YELISYVKDRLRLSFFNDKRSWSYREAKEISWELMKEIYYRLDELEKLKESLSRGILIDW
NEVAKRIEEVAEETGIRADELLEYIEGKRKLSFKDYIKIAKVLGIDVEHTIEAMRVFARK
YSSYAEIGRRLGTWNSSVKTILESNAVNVEILERIRKIELELIEEILSDEKLKEGIAYLI
FLSQNELYWDEITKVEELRGEFIIYDLHVPGYHNFIAGNMPTVVHNTTAALALSRELFGE
NWRHNFLELNASDERGINVIREKVKEFARTKPIGGASFKIIFLDEADALTQDAQQALRRT
MEMFSSNVRFILSCNYSSKIIEPIQSRCAIFRFRPLRDEDIAKRLRYIAENEGLELTEEG
LQAILYIAEGDMRRAINILQAAAALDKKITDENVFMVASRARPEDIREMMLLALKGNFLK
AREKLREILLKQGLSGEDVLIQMHKEVFNLPIDEPTKVYLADKIGEYNFRLVEGANEMIQ
LEALLAQFTLVGKKK

SEQUENCE LISTING

```
<160> NUMBER OF SEQ ID NOS: 37

<210> SEQ ID NO 1
<211> LENGTH: 4305
<212> TYPE: DNA
<213> ORGANISM: Pyrococcus horikoshii
<220> FEATURE:
<223> OTHER INFORMATION: polD large subunit

<400> SEQUENCE: 1
gtggtgctga tggagcttcc aaaggaaatg gaagagtact tttccatgtt acagagggag      60
atagataaag cttatgagat agccaagaag gctagagctc agggtaagga tcctagcttg     120
gatgttgaga tccctcaagc ttctgacatg gccggaagag ttgaaagctt agtcggcccc     180
ccaggagttg ccgaaagaat tagggagcta gttaaggaat atggtaagga gatagctgct     240
ctcaaaatag ttgatgagat aatagatgga aaattcggtg atctgggaag taaggaaaag     300
tatgctgaac aggccgtaag gacggccctt gccatactaa ctgaaggtgt agtttccgct     360
ccaattgagg gaatagctag tgttaagata aagaggaaca catggtccga taattctgag     420
tatttagctc tctactatgc tgggccaatc agaagctctg gaggaacggc ccaagcgcta     480
agtgttctcg ttggcgacta cgtgaggaga aagctaggcc ttgatagatt taagccaagt     540
gaaaagcaca tagaaagaat ggttgaggaa gttgatctct atcataggac tgtttctaga     600
ctacagtatc atccttcccc agaggaagta aggttagcta tgaggaatat tccaattgaa     660
attactggag aagctacgga tgaagttgaa gtttctcaca gagatatccc tggagtggaa     720
accaaccaac ttagggggtgg tgctattcta gtcctagcgg agggagttct tcagaaggcc     780
aagaagttag ttaaatatat agataagatg ggaattgaag gttgggagtg gcttaaagaa     840
ttcgtcgaag ctaggaaaa gggagaagaa attgaagagg aaggatctgc tgaatcaaca     900
gttgaagaga caaaggtaga agttgacatg ggcttttact actctctcta tcagaagttc     960
```

-continued

```
aaatctgaga ttgctccaaa tgataagtat gctaaggaaa taataggtgg gagacctctc    1020
ttctcagatc cctccaggaa tggaggattt aggctacgct atggaaggag cagggtgagt    1080
ggatttgcaa cttggggaat aaatccagcg acaatgattt tagttgatga gttcttagcc    1140
attgggactc aattaaagac tgagagacca ggaaagggcg ctgtggtaac tcctgtaact    1200
actatagagg gcccaatagt caagctcaag gatggtagcg tagtgaaggt tgacgattac    1260
aagctagccc tcaagatcag ggatgaagtt gaggagatct tatacttagg ggatgctgtc    1320
attgcttttg gtgacttcgt tgagaataat cagaccctcc ttccggccaa ttattgcgaa    1380
gagtggtgga tactggaatt tacgaaggct ctcaatgaaa tttatgaagt ggagcttaaa    1440
ccatttgaag ttaattcgag tgaagatctt gaggaagcgg cagattatct cgaggttgac    1500
attgaatttt tgaaagagct acttaaggat cccttaagga ctaagcctcc agttgagctt    1560
gctattcatt tctccgaaat acttgggata ccccttcatc cgtattatac cctctattgg    1620
aattccgtga agcccgagca agtggagaag ctttggaggg tgctcaagga acacgctcat    1680
atcgactggg ataacttcag gggaattaag tttgccagga ggatagttat accccctagaa   1740 aaacttagag attctaagag agcccttgag ctcctgggac ttccacataa ggtggagggt    1800
aaaaacgtta tcgttgatta tccctgggct gcagctctat taactcccct tggcaatctt    1860
gagtgggagt tcagagctaa acctttacac acgaccatag atatcataaa cgaaaacaat    1920
gagattaagc ttagggatag gggaataagc tggatagggg ccaggatggg gaggcccgag    1980
aaagctaagg agagaaagat gaagcctcct gttcaagttc tcttcccaat aggacttgct    2040
ggtggaagta gtagagatat aaagaaggcc gctgaggagg gtaaggttgc cgaggttgaa    2100
atagccctct tcaagtgccc caaatgtggt cacgttggcc ctgagcatat ctgtcccaac    2160
tgtggaacca ggaaggaatt gatctgggta tgccctaggt gtaacgcgga gtaccccgag    2220
agccaggcaa gtggctataa ctacacctgt ccaaagtgca acgttaagct aaagccttat    2280
gctaagagaa agataaagcc atcagagttg cttaagaggg ccatggataa tgtcaaagtt    2340
tatggcattg acaagctgaa gggagttatg ggaatgacat ccggctggaa aatgccggaa    2400
cctctggaga aaggacttct tagggctaaa aatgatgtat atgtgtttaa agatgggaca    2460
attaggtttg acgccactga tgctccaata acccatttta gacccagaga aattggagtt    2520
tcagttgaga aacttagaga gctggggtat acccacgact tcgagggtaa tcccttggtt    2580
agcgaagatc agatagttga gcttaagcct caggatatta tactctccaa agaagcaggt    2640
aaataccttt tgaaagttgc aaagttcgtt gatgacctcc ttgagaagtt ttatggtctt    2700
ccaaggttct acaatgctga gaagatggaa gatctaattg gacatttggt gatagggctt    2760
gctcctcaca cttccgctgg aatcgtcgga aggatcatag ggttcgttga tgccttggtt    2820
ggttatgctc atccctactt ccacgctgca aagaggagaa attgcttccc gggagataca    2880
agaatattag ttcaaattaa tggaactccg cagagagtta cacttaagga attatatgag    2940
ctctttgacg aggaacatta tgaaagcatg gtgtacgtaa ggaaaaagcc aaaggtagac    3000
attaaggtat actccttcaa ccctgaggaa ggtaaggtag ttctgaccga tattgaggag    3060
gtaataaaag cccctgctac tgatcattta attcgctttg aacttgagct cggaagtagc    3120
tttgagacaa ccgtggatca cccagtcctc gtatatgaaa atgaaagttc cgtggagaaa    3180
agggcatttg aggttaggga ggggaatata ataattataa tcgatgaatc aactttggaa    3240
ccccttaagg ttgctgttaa aaaaatagag ttcatagaac cgcctgagga ctttgtgttc    3300
tctcttaatg ctaaaaaata tcatactgta ataattaatg aaaatattgt gacgcatcag    3360
```

-continued

```
tgcgatggtg atgaagatgc tgtcatgttg ctcctggatg ctttactaaa cttttcccgc    3420
tattatcttc cagagaagcg tggtggaaag atggatgccc cattggtcat cacaacgcgc    3480
ttagatccga gggaagttga tagcgaggtt cataacatgg atatagtcag gtactatcct    3540
ctcgagtttt atgaggctac ctacgaactt aagtctccaa aggagttggt aggagttatt    3600
gagagagtcg aggatagatt gggaaaacct gaaatgtatt atgggctgaa gttcacccac    3660
gacacggatg atatagccct cggccctaag atgagccttt acaagcaatt gggagatatg    3720
gaagaaaaag tgaagaggca acttgacgtc gccaggagga tcagggccgt tgatgagcat    3780
aaagttgctg agacgatact caattctcat ttgatccctg atcttagggg taatttgaga    3840
agctttacta ggcaggagtt ccgttgtgtg aagtgcaaca caaagtttag agacctccc     3900 ctcgatggta atgtccaat  ttgcggagga aaaatagtgc tcaccgttag taaaggggcc    3960
atagagaagt atcttgggac ggctaagatg ctggtgacgg agtacaaagt taaaaactat    4020
acgaggcaga ggatatgctt aaccgagagg gatatagatt ccctgtttga aactgtattt    4080
ccggagactc agttaacgct tctcgttaat cccaatgaca tatgtcagag aattatcatg    4140
gaaaggactg gagggagcaa aaaatcgggc ctcctagaaa actttgctaa cggttataat    4200
aaggggaaga aagaagaaat gcctaaaaag caaagaaaga aggagcagga aaagtcaaag    4260
aaaagaaaag taattagcct agatgatttc ttctcaagga aataa                   4305
```

<210> SEQ ID NO 2
<211> LENGTH: 1434
<212> TYPE: PRT
<213> ORGANISM: Pyrococcus horikoshii
<220> FEATURE:
<223> OTHER INFORMATION: polD large subunit

<400> SEQUENCE: 2

```
Met Val Leu Met Glu Leu Pro Lys Glu Met Glu Glu Tyr Phe Ser Met
1               5                   10                  15

Leu Gln Arg Glu Ile Asp Lys Ala Tyr Glu Ile Ala Lys Lys Ala Arg
            20                  25                  30

Ala Gln Gly Lys Asp Pro Ser Leu Asp Val Glu Ile Pro Gln Ala Ser
        35                  40                  45

Asp Met Ala Gly Arg Val Glu Ser Leu Val Gly Pro Gly Val Ala
    50                  55                  60

Glu Arg Ile Arg Glu Leu Val Lys Glu Tyr Gly Lys Glu Ile Ala Ala
65                  70                  75                  80

Leu Lys Ile Val Asp Glu Ile Ile Asp Gly Lys Phe Gly Asp Leu Gly
                85                  90                  95

Ser Lys Glu Lys Tyr Ala Glu Gln Ala Val Arg Thr Ala Leu Ala Ile
            100                 105                 110

Leu Thr Glu Gly Val Val Ser Ala Pro Ile Glu Gly Ile Ala Ser Val
        115                 120                 125

Lys Ile Lys Arg Asn Thr Trp Ser Asp Asn Ser Glu Tyr Leu Ala Leu
    130                 135                 140

Tyr Tyr Ala Gly Pro Ile Arg Ser Ser Gly Gly Thr Ala Gln Ala Leu
145                 150                 155                 160

Ser Val Leu Val Gly Asp Tyr Val Arg Lys Leu Gly Leu Asp Arg
                165                 170                 175

Phe Lys Pro Ser Glu Lys His Ile Glu Arg Met Val Glu Glu Val Asp
            180                 185                 190
```

```
Leu Tyr His Arg Thr Val Ser Arg Leu Gln Tyr His Pro Ser Pro Glu
        195                 200                 205

Glu Val Arg Leu Ala Met Arg Asn Ile Pro Ile Glu Ile Thr Gly Glu
        210                 215                 220

Ala Thr Asp Glu Val Glu Val Ser His Arg Asp Ile Pro Gly Val Glu
225                 230                 235                 240

Thr Asn Gln Leu Arg Gly Gly Ala Ile Leu Val Leu Ala Glu Gly Val
                245                 250                 255

Leu Gln Lys Ala Lys Lys Leu Val Lys Tyr Ile Asp Lys Met Gly Ile
                260                 265                 270

Glu Gly Trp Glu Trp Leu Lys Glu Phe Val Glu Ala Lys Glu Lys Gly
            275                 280                 285

Glu Glu Ile Glu Glu Gly Ser Ala Glu Ser Thr Val Glu Glu Thr
            290                 295                 300

Lys Val Glu Val Asp Met Gly Phe Tyr Tyr Ser Leu Tyr Gln Lys Phe
305                 310                 315                 320

Lys Ser Glu Ile Ala Pro Asn Asp Lys Tyr Ala Lys Glu Ile Ile Gly
                325                 330                 335

Gly Arg Pro Leu Phe Ser Asp Pro Ser Arg Asn Gly Gly Phe Arg Leu
                340                 345                 350

Arg Tyr Gly Arg Ser Arg Val Ser Gly Phe Ala Thr Trp Gly Ile Asn
            355                 360                 365

Pro Ala Thr Met Ile Leu Val Asp Glu Phe Leu Ala Ile Gly Thr Gln
            370                 375                 380

Leu Lys Thr Glu Arg Pro Gly Lys Gly Ala Val Val Thr Pro Val Thr
385                 390                 395                 400

Thr Ile Glu Gly Pro Ile Val Lys Leu Lys Asp Gly Ser Val Val Lys
                405                 410                 415

Val Asp Asp Tyr Lys Leu Ala Leu Lys Ile Arg Asp Glu Val Glu Glu
                420                 425                 430

Ile Leu Tyr Leu Gly Asp Ala Val Ile Ala Phe Gly Asp Phe Val Glu
            435                 440                 445

Asn Asn Gln Thr Leu Leu Pro Ala Asn Tyr Cys Glu Glu Trp Trp Ile
            450                 455                 460

Leu Glu Phe Thr Lys Ala Leu Asn Glu Ile Tyr Glu Val Glu Leu Lys
465                 470                 475                 480

Pro Phe Glu Val Asn Ser Ser Glu Asp Leu Glu Glu Ala Ala Asp Tyr
                485                 490                 495

Leu Glu Val Asp Ile Glu Phe Leu Lys Glu Leu Leu Lys Asp Pro Leu
                500                 505                 510

Arg Thr Lys Pro Pro Val Glu Leu Ala Ile His Phe Ser Glu Ile Leu
            515                 520                 525

Gly Ile Pro Leu His Pro Tyr Tyr Thr Leu Tyr Trp Asn Ser Val Lys
            530                 535                 540

Pro Glu Gln Val Glu Lys Leu Trp Arg Val Leu Lys Glu His Ala His
545                 550                 555                 560

Ile Asp Trp Asp Asn Phe Arg Gly Ile Lys Phe Ala Arg Arg Ile Val
                565                 570                 575

Ile Pro Leu Glu Lys Leu Arg Asp Ser Lys Arg Ala Leu Glu Leu Leu
                580                 585                 590

Gly Leu Pro His Lys Val Glu Gly Lys Asn Val Ile Val Asp Tyr Pro
            595                 600                 605

Trp Ala Ala Ala Leu Leu Thr Pro Leu Gly Asn Leu Glu Trp Glu Phe
```

-continued

```
            610                 615                 620
Arg Ala Lys Pro Leu His Thr Thr Ile Asp Ile Ile Asn Glu Asn Asn
625                 630                 635                 640

Glu Ile Lys Leu Arg Asp Arg Gly Ile Ser Trp Ile Gly Ala Arg Met
                    645                 650                 655

Gly Arg Pro Glu Lys Ala Lys Glu Arg Lys Met Lys Pro Pro Val Gln
                660                 665                 670

Val Leu Phe Pro Ile Gly Leu Ala Gly Gly Ser Ser Arg Asp Ile Lys
            675                 680                 685

Lys Ala Ala Glu Glu Gly Lys Val Ala Glu Val Glu Ile Ala Leu Phe
690                 695                 700

Lys Cys Pro Lys Cys Gly His Val Gly Pro Glu His Ile Cys Pro Asn
705                 710                 715                 720

Cys Gly Thr Arg Lys Glu Leu Ile Trp Val Cys Pro Arg Cys Asn Ala
                    725                 730                 735

Glu Tyr Pro Glu Ser Gln Ala Ser Gly Tyr Asn Tyr Thr Cys Pro Lys
                740                 745                 750

Cys Asn Val Lys Leu Lys Pro Tyr Ala Lys Arg Lys Ile Lys Pro Ser
            755                 760                 765

Glu Leu Leu Lys Arg Ala Met Asp Asn Val Lys Val Tyr Gly Ile Asp
770                 775                 780

Lys Leu Lys Gly Val Met Gly Met Thr Ser Gly Trp Lys Met Pro Glu
785                 790                 795                 800

Pro Leu Glu Lys Gly Leu Leu Arg Ala Lys Asn Asp Val Tyr Val Phe
                805                 810                 815

Lys Asp Gly Thr Ile Arg Phe Asp Ala Thr Asp Ala Pro Ile Thr His
                820                 825                 830

Phe Arg Pro Arg Glu Ile Gly Val Ser Val Glu Lys Leu Arg Glu Leu
            835                 840                 845

Gly Tyr Thr His Asp Phe Glu Gly Asn Pro Leu Val Ser Glu Asp Gln
850                 855                 860

Ile Val Glu Leu Lys Pro Gln Asp Ile Ile Leu Ser Lys Glu Ala Gly
865                 870                 875                 880

Lys Tyr Leu Leu Lys Val Ala Lys Phe Val Asp Asp Leu Leu Glu Lys
                885                 890                 895

Phe Tyr Gly Leu Pro Arg Phe Tyr Asn Ala Glu Lys Met Glu Asp Leu
                900                 905                 910

Ile Gly His Leu Val Ile Gly Leu Ala Pro His Thr Ser Ala Gly Ile
            915                 920                 925

Val Gly Arg Ile Ile Gly Phe Val Asp Ala Leu Val Gly Tyr Ala His
930                 935                 940

Pro Tyr Phe His Ala Ala Lys Arg Arg Asn Cys Phe Pro Gly Asp Thr
945                 950                 955                 960

Arg Ile Leu Val Gln Ile Asn Gly Thr Pro Gln Arg Val Thr Leu Lys
                965                 970                 975

Glu Leu Tyr Glu Leu Phe Asp Glu Glu His Tyr Glu Ser Met Val Tyr
                980                 985                 990

Val Arg Lys Lys Pro Lys Val Asp Ile Lys Val Tyr Ser Phe Asn Pro
            995                 1000                1005

Glu Glu Gly Lys Val Val Leu Thr Asp Ile Glu Glu Val Ile Lys
    1010                1015                1020

Ala Pro Ala Thr Asp His Leu Ile Arg Phe Glu Leu Glu Leu Gly
    1025                1030                1035
```

-continued

```
Ser Ser Phe Glu Thr Thr Val Asp His Pro Val Leu Val Tyr Glu
    1040            1045                1050

Asn Gly Lys Phe Val Glu Lys Arg Ala Phe Glu Val Arg Glu Gly
    1055            1060                1065

Asn Ile Ile Ile Ile Ile Asp Glu Ser Thr Leu Glu Pro Leu Lys
    1070            1075                1080

Val Ala Val Lys Lys Ile Glu Phe Ile Glu Pro Pro Glu Asp Phe
    1085            1090                1095

Val Phe Ser Leu Asn Ala Lys Lys Tyr His Thr Val Ile Ile Asn
    1100            1105                1110

Glu Asn Ile Val Thr His Gln Cys Asp Gly Asp Glu Asp Ala Val
    1115            1120                1125

Met Leu Leu Leu Asp Ala Leu Leu Asn Phe Ser Arg Tyr Tyr Leu
    1130            1135                1140

Pro Glu Lys Arg Gly Gly Lys Met Asp Ala Pro Leu Val Ile Thr
    1145            1150                1155

Thr Arg Leu Asp Pro Arg Glu Val Asp Ser Glu Val His Asn Met
    1160            1165                1170

Asp Ile Val Arg Tyr Tyr Pro Leu Glu Phe Tyr Glu Ala Thr Tyr
    1175            1180                1185

Glu Leu Lys Ser Pro Lys Glu Leu Val Gly Val Ile Glu Arg Val
    1190            1195                1200

Glu Asp Arg Leu Gly Lys Pro Glu Met Tyr Tyr Gly Leu Lys Phe
    1205            1210                1215

Thr His Asp Thr Asp Asp Ile Ala Leu Gly Pro Lys Met Ser Leu
    1220            1225                1230

Tyr Lys Gln Leu Gly Asp Met Glu Glu Lys Val Lys Arg Gln Leu
    1235            1240                1245

Asp Val Ala Arg Arg Ile Arg Ala Val Asp Glu His Lys Val Ala
    1250            1255                1260

Glu Thr Ile Leu Asn Ser His Leu Ile Pro Asp Leu Arg Gly Asn
    1265            1270                1275

Leu Arg Ser Phe Thr Arg Gln Glu Phe Arg Cys Val Lys Cys Asn
    1280            1285                1290

Thr Lys Phe Arg Arg Pro Pro Leu Asp Gly Lys Cys Pro Ile Cys
    1295            1300                1305

Gly Gly Lys Ile Val Leu Thr Val Ser Lys Gly Ala Ile Glu Lys
    1310            1315                1320

Tyr Leu Gly Thr Ala Lys Met Leu Val Thr Glu Tyr Lys Val Lys
    1325            1330                1335

Asn Tyr Thr Arg Gln Arg Ile Cys Leu Thr Glu Arg Asp Ile Asp
    1340            1345                1350

Ser Leu Phe Glu Thr Val Phe Pro Glu Thr Gln Leu Thr Leu Leu
    1355            1360                1365

Val Asn Pro Asn Asp Ile Cys Gln Arg Ile Ile Met Glu Arg Thr
    1370            1375                1380

Gly Gly Ser Lys Lys Ser Gly Leu Leu Glu Asn Phe Ala Asn Gly
    1385            1390                1395

Tyr Asn Lys Gly Lys Lys Glu Met Pro Lys Lys Gln Arg Lys
    1400            1405                1410

Lys Glu Gln Glu Lys Ser Lys Arg Lys Val Ile Ser Leu Asp
    1415            1420                1425
```

Asp Phe  Phe Ser Arg Lys
    1430

<210> SEQ ID NO 3
<211> LENGTH: 3807
<212> TYPE: DNA
<213> ORGANISM: Pyrococcus horikoshii
<220> FEATURE:
<223> OTHER INFORMATION: polD large subunit-intein

<400> SEQUENCE: 3

| | | | | | |
|---|---|---|---|---|---|
| gtggtgctga | tggagcttcc | aaaggaaatg | aagagtact | tttccatgtt | acagagggag | 60 |
| atagataaag | cttatgagat | agccaagaag | gctagagctc | agggtaagga | tcctagcttg | 120 |
| gatgttgaga | tccctcaagc | ttctgacatg | gccggaagag | ttgaaagctt | agtcggcccc | 180 |
| ccaggagttg | ccgaaagaat | tagggagcta | gttaaggaat | atggtaagga | gatagctgct | 240 |
| ctcaaaatag | ttgatgagat | aatagatgga | aaattcggtg | atctgggaag | taaggaaaag | 300 |
| tatgctgaac | aggccgtaag | gacggccctt | gccatactaa | ctgaaggtgt | agtttccgct | 360 |
| ccaattgagg | gaatagctag | tgttaagata | aagaggaaca | catggtccga | taattctgag | 420 |
| tatttagctc | tctactatgc | tgggccaatc | agaagctctg | gaggaacggc | ccaagcgcta | 480 |
| agtgttctcg | ttggcgacta | cgtgaggaga | aagctaggcc | ttgatagatt | taagccaagt | 540 |
| gaaaagcaca | tagaaagaat | ggttgaggaa | gttgatctct | atcataggac | tgtttctaga | 600 |
| ctacagtatc | atccttcccc | agaggaagta | aggttagcta | tgaggaatat | tccaattgaa | 660 |
| attactggag | aagctacgga | tgaagttgaa | gtttctcaca | gagatatccc | tggagtggaa | 720 |
| accaaccaac | ttaggggtgg | tgctattcta | gtcctagcgg | agggagttct | tcagaaggcc | 780 |
| aagaagttag | ttaaatatat | agataagatg | ggaattgaag | gttgggagtg | gcttaaagaa | 840 |
| ttcgtcgaag | ctaaggaaaa | gggagaagaa | attgaagagg | aaggatctgc | tgaatcaaca | 900 |
| gttgaagaga | caaaggtaga | agttgacatg | ggcttttact | actctctcta | tcagaagttc | 960 |
| aaatctgaga | ttgctccaaa | tgataagtat | gctaaggaaa | taataggtgg | gagacctctc | 1020 |
| ttctcagatc | cctccaggaa | tggaggattt | aggctacgct | atggaaggag | cagggtgagt | 1080 |
| ggatttgcaa | cttggggaat | aaatccagcg | acaatgattt | tagttgatga | gttcttagcc | 1140 |
| attgggactc | aattaaagac | tgagagacca | ggaaagggcg | ctgtggtaac | tcctgtaact | 1200 |
| actatagagg | gcccaatagt | caagctcaag | gatggtagcg | tagtgaaggt | tgacgattac | 1260 |
| aagctagccc | tcaagatcag | ggatgaagtt | gaggagatct | tatacttagg | ggatgctgtc | 1320 |
| attgcttttg | gtgacttcgt | tgagaataat | cagaccctcc | ttccggccaa | ttattgcgaa | 1380 |
| gagtggtgga | tactggaatt | tacgaaggct | ctcaatgaaa | tttatgaagt | ggagcttaaa | 1440 |
| ccatttgaag | ttaattcgag | tgaagatctt | gaggaagcgg | cagattatct | cgaggttgac | 1500 |
| attgaatttt | tgaaagagct | acttaaggat | cccttaagga | ctaagcctcc | agttgagctt | 1560 |
| gctattcatt | tctccgaaat | acttgggata | ccccttcatc | cgtattatac | cctctattgg | 1620 |
| aattccgtga | agcccgagca | agtggagaag | ctttggaggg | tgctcaagga | acacgctcat | 1680 |
| atcgactggg | ataacttcag | gggaattaag | tttgccagga | ggatagttat | accccctagaa | 1740 |
| aaacttagag | attctaagag | agcccttgag | ctccctgggac | ttccacataa | ggtgagggt | 1800 |
| aaaaacgtta | tcgttgatta | tccctgggct | gcagctctat | taactcccct | tggcaatctt | 1860 |
| gagtgggagt | tcagagctaa | acctttacac | acgaccatag | atatcataaa | cgaaaacaat | 1920 |
| gagattaagc | ttagggatag | gggaataagc | tggataggggg | ccaggatggg | gaggcccgag | 1980 |

-continued

```
aaagctaagg agagaaagat gaagcctcct gttcaagttc tcttcccaat aggacttgct  2040
ggtggaagta gtagagatat aaagaaggcc gctgaggagg gtaaggttgc cgaggttgaa  2100
atagccctct tcaagtgccc caaatgtggt cacgttggcc ctgagcatat ctgtcccaac  2160
tgtggaacca ggaaggaatt gatctgggta tgccctaggt gtaacgcgga gtaccccgag  2220
agccaggcaa gtggctataa ctacacctgt ccaaagtgca acgttaagct aaagccttat  2280
gctaagagaa agataaagcc atcagagttg cttaagaggg ccatggataa tgtcaaagtt  2340
tatggcattg acaagctgaa gggagttatg ggaatgacat ccggctggaa aatgccggaa  2400
cctctggaga aaggacttct tagggctaaa aatgatgtat atgtgtttaa agatgggaca  2460
attaggtttg acgccactga tgctccaata acccatttta gacccagaga aattggagtt  2520
tcagttgaga aacttagaga gctggggtat acccacgact cgagggtaa tcccttggtt  2580
agcgaagatc agatagttga gcttaagcct caggatatta tactctccaa agaagcaggt  2640
aaataccttt tgaaagttgc aaagttcgtt gatgacctcc ttgagaagtt ttatggtctt  2700
ccaaggttct acaatgctga gaagatggaa gatctaattg acatttggt gatagggctt  2760
gctcctcaca cttccgctgg aatcgtcgga aggatcatag ggttcgttga tgccttggtt  2820
ggttatgctc atccctactt ccacgctgca aagaggagaa attgcgatgg tgatgaagat  2880
gctgtcatgt tgctcctgga tgctttacta aactttttccc gctattatct tccagagaag  2940
cgtggtggaa agatggatgc cccattggtc atcacaacgc gcttagatcc gagggaagtt  3000
gatagcgagg ttcataacat ggatatagtc aggtactatc ctctcgagtt ttatgaggct  3060
acctacgaac ttaagtctcc aaaggagttg gtaggagtta ttgagagagt cgaggataga  3120
ttgggaaaac ctgaaatgta ttatgggctg aagttcaccc acgacacgga tgatatagcc  3180
ctcggcccta agatgagcct ttacaagcaa ttgggagata tggaagaaaa agtgaagagg  3240
caacttgacg tcgccaggag gatcagggcc gttgatgagc ataaagttgc tgagacgata  3300
ctcaattctc atttgatccc tgatcttagg ggtaatttga gaagctttac taggcaggag  3360
ttccgttgtg tgaagtgcaa cacaaagttt aggagacctc ccctcgatgg taaatgtcca  3420
atttgcggag gaaaaatagt gctcaccgtt agtaaggggg ccatagagaa gtatcttggg  3480
acggctaaga tgctggtgac ggagtacaaa gttaaaaact atacgaggca gaggatatgc  3540
ttaaccgaga gggatataga ttccctgttt gaaactgtat ttccggagac tcagttaacg  3600
cttctcgtta atcccaatga catatgtcag agaattatca tggaaaggac tggagggagc  3660
aaaaaatcgg gcctcctaga aaactttgct aacggttata ataaggggaa gaaagaagaa  3720
atgcctaaaa agcaaagaaa gaaggagcag gaaaagtcaa agaaaagaaa agtaattagc  3780
ctagatgatt tcttctcaag gaaataa                                     3807
```

<210> SEQ ID NO 4
<211> LENGTH: 1268
<212> TYPE: PRT
<213> ORGANISM: Pyrococcus horikoshii
<220> FEATURE:
<223> OTHER INFORMATION: polD large subunit-intein

<400> SEQUENCE: 4

Met Val Leu Met Glu Leu Pro Lys Glu Met Glu Glu Tyr Phe Ser Met
1               5                   10                  15

Leu Gln Arg Glu Ile Asp Lys Ala Tyr Glu Ile Ala Lys Lys Ala Arg
            20                  25                  30

Ala Gln Gly Lys Asp Pro Ser Leu Asp Val Glu Ile Pro Gln Ala Ser

-continued

```
                35                  40                  45
Asp Met Ala Gly Arg Val Glu Ser Leu Val Gly Pro Pro Gly Val Ala
 50                  55                  60

Glu Arg Ile Arg Glu Leu Val Lys Glu Tyr Gly Lys Glu Ile Ala Ala
 65                  70                  75                  80

Leu Lys Ile Val Asp Glu Ile Ile Asp Gly Lys Phe Gly Asp Leu Gly
                 85                  90                  95

Ser Lys Glu Lys Tyr Ala Glu Gln Ala Val Arg Thr Ala Leu Ala Ile
                100                 105                 110

Leu Thr Glu Gly Val Val Ser Ala Pro Ile Glu Gly Ile Ala Ser Val
                115                 120                 125

Lys Ile Lys Arg Asn Thr Trp Ser Asp Asn Ser Glu Tyr Leu Ala Leu
130                 135                 140

Tyr Tyr Ala Gly Pro Ile Arg Ser Ser Gly Gly Thr Ala Gln Ala Leu
145                 150                 155                 160

Ser Val Leu Val Gly Asp Tyr Val Arg Arg Lys Leu Gly Leu Asp Arg
                165                 170                 175

Phe Lys Pro Ser Glu Lys His Ile Glu Arg Met Val Glu Glu Val Asp
                180                 185                 190

Leu Tyr His Arg Thr Val Ser Arg Leu Gln Tyr His Pro Ser Pro Glu
                195                 200                 205

Glu Val Arg Leu Ala Met Arg Asn Ile Pro Ile Glu Ile Thr Gly Glu
                210                 215                 220

Ala Thr Asp Glu Val Glu Val Ser His Arg Asp Ile Pro Gly Val Glu
225                 230                 235                 240

Thr Asn Gln Leu Arg Gly Gly Ala Ile Leu Val Leu Ala Glu Gly Val
                245                 250                 255

Leu Gln Lys Ala Lys Lys Leu Val Lys Tyr Ile Asp Lys Met Gly Ile
                260                 265                 270

Glu Gly Trp Glu Trp Leu Lys Glu Phe Val Glu Ala Lys Glu Lys Gly
                275                 280                 285

Glu Glu Ile Glu Glu Gly Ser Ala Glu Ser Thr Val Glu Glu Thr
                290                 295                 300

Lys Val Glu Val Asp Met Gly Phe Tyr Tyr Ser Leu Tyr Gln Lys Phe
305                 310                 315                 320

Lys Ser Glu Ile Ala Pro Asn Asp Lys Tyr Ala Lys Glu Ile Ile Gly
                325                 330                 335

Gly Arg Pro Leu Phe Ser Asp Pro Ser Arg Asn Gly Gly Phe Arg Leu
                340                 345                 350

Arg Tyr Gly Arg Ser Arg Val Ser Gly Phe Ala Thr Trp Gly Ile Asn
                355                 360                 365

Pro Ala Thr Met Ile Leu Val Asp Glu Phe Leu Ala Ile Gly Thr Gln
                370                 375                 380

Leu Lys Thr Glu Arg Pro Gly Lys Gly Ala Val Val Thr Pro Val Thr
385                 390                 395                 400

Thr Ile Glu Gly Pro Ile Val Lys Leu Lys Asp Gly Ser Val Val Lys
                405                 410                 415

Val Asp Asp Tyr Lys Leu Ala Leu Lys Ile Arg Asp Glu Val Glu Glu
                420                 425                 430

Ile Leu Tyr Leu Gly Asp Ala Val Ile Ala Phe Gly Asp Phe Val Glu
                435                 440                 445

Asn Asn Gln Thr Leu Leu Pro Ala Asn Tyr Cys Glu Glu Trp Trp Ile
450                 455                 460
```

-continued

```
Leu Glu Phe Thr Lys Ala Leu Asn Glu Ile Tyr Glu Val Glu Leu Lys
465                 470                 475                 480

Pro Phe Glu Val Asn Ser Ser Glu Asp Leu Glu Glu Ala Ala Asp Tyr
                485                 490                 495

Leu Glu Val Asp Ile Glu Phe Leu Lys Glu Leu Leu Lys Asp Pro Leu
            500                 505                 510

Arg Thr Lys Pro Pro Val Glu Leu Ala Ile His Phe Ser Glu Ile Leu
        515                 520                 525

Gly Ile Pro Leu His Pro Tyr Tyr Thr Leu Tyr Trp Asn Ser Val Lys
    530                 535                 540

Pro Glu Gln Val Glu Lys Leu Trp Arg Val Leu Lys Glu His Ala His
545                 550                 555                 560

Ile Asp Trp Asp Asn Phe Arg Gly Ile Lys Phe Ala Arg Arg Ile Val
                565                 570                 575

Ile Pro Leu Glu Lys Leu Arg Asp Ser Lys Arg Ala Leu Glu Leu Leu
            580                 585                 590

Gly Leu Pro His Lys Val Glu Gly Lys Asn Val Ile Val Asp Tyr Pro
        595                 600                 605

Trp Ala Ala Leu Leu Thr Pro Leu Gly Asn Leu Glu Trp Glu Phe
    610                 615                 620

Arg Ala Lys Pro Leu His Thr Thr Ile Asp Ile Ile Asn Glu Asn Asn
625                 630                 635                 640

Glu Ile Lys Leu Arg Asp Arg Gly Ile Ser Trp Ile Gly Ala Arg Met
                645                 650                 655

Gly Arg Pro Glu Lys Ala Lys Glu Arg Lys Met Lys Pro Pro Val Gln
            660                 665                 670

Val Leu Phe Pro Ile Gly Leu Ala Gly Gly Ser Ser Arg Asp Ile Lys
        675                 680                 685

Lys Ala Ala Glu Glu Gly Lys Val Ala Glu Val Glu Ile Ala Leu Phe
    690                 695                 700

Lys Cys Pro Lys Cys Gly His Val Gly Pro Glu His Ile Cys Pro Asn
705                 710                 715                 720

Cys Gly Thr Arg Lys Glu Leu Ile Trp Val Cys Pro Arg Cys Asn Ala
                725                 730                 735

Glu Tyr Pro Glu Ser Gln Ala Ser Gly Tyr Asn Tyr Thr Cys Pro Lys
            740                 745                 750

Cys Asn Val Lys Leu Lys Pro Tyr Ala Lys Arg Lys Ile Lys Pro Ser
        755                 760                 765

Glu Leu Leu Lys Arg Ala Met Asp Asn Val Lys Val Tyr Gly Ile Asp
    770                 775                 780

Lys Leu Lys Gly Val Met Gly Met Thr Ser Gly Trp Lys Met Pro Glu
785                 790                 795                 800

Pro Leu Glu Lys Gly Leu Leu Arg Ala Lys Asn Asp Val Tyr Val Phe
                805                 810                 815

Lys Asp Gly Thr Ile Arg Phe Asp Ala Thr Asp Ala Pro Ile Thr His
            820                 825                 830

Phe Arg Pro Arg Glu Ile Gly Val Ser Val Glu Lys Leu Arg Glu Leu
        835                 840                 845

Gly Tyr Thr His Asp Phe Glu Gly Asn Pro Leu Val Ser Glu Asp Gln
    850                 855                 860

Ile Val Glu Leu Lys Pro Gln Asp Ile Ile Leu Ser Lys Glu Ala Gly
865                 870                 875                 880
```

-continued

```
Lys Tyr Leu Leu Lys Val Ala Lys Phe Val Asp Asp Leu Leu Glu Lys
            885                 890                 895

Phe Tyr Gly Leu Pro Arg Phe Tyr Asn Ala Glu Lys Met Glu Asp Leu
            900                 905                 910

Ile Gly His Leu Val Ile Gly Leu Ala Pro His Thr Ser Ala Gly Ile
            915                 920                 925

Val Gly Arg Ile Ile Gly Phe Val Asp Ala Leu Val Gly Tyr Ala His
            930                 935                 940

Pro Tyr Phe His Ala Ala Lys Arg Arg Asn Cys Asp Gly Asp Glu Asp
945                 950                 955                 960

Ala Val Met Leu Leu Leu Asp Ala Leu Leu Asn Phe Ser Arg Tyr Tyr
                    965                 970                 975

Leu Pro Glu Lys Arg Gly Gly Lys Met Asp Ala Pro Leu Val Ile Thr
            980                 985                 990

Thr Arg Leu Asp Pro Arg Glu Val Asp Ser Glu Val His Asn Met Asp
            995                 1000                1005

Ile Val Arg Tyr Tyr Pro Leu Glu Phe Tyr Glu Ala Thr Tyr Glu
    1010                1015                1020

Leu Lys Ser Pro Lys Glu Leu Val Gly Val Ile Glu Arg Val Glu
    1025                1030                1035

Asp Arg Leu Gly Lys Pro Glu Met Tyr Tyr Gly Leu Lys Phe Thr
    1040                1045                1050

His Asp Thr Asp Asp Ile Ala Leu Gly Pro Lys Met Ser Leu Tyr
    1055                1060                1065

Lys Gln Leu Gly Asp Met Glu Glu Lys Val Lys Arg Gln Leu Asp
    1070                1075                1080

Val Ala Arg Arg Ile Arg Ala Val Asp Glu His Lys Val Ala Glu
    1085                1090                1095

Thr Ile Leu Asn Ser His Leu Ile Pro Asp Leu Arg Gly Asn Leu
    1100                1105                1110

Arg Ser Phe Thr Arg Gln Glu Phe Arg Cys Val Lys Cys Asn Thr
    1115                1120                1125

Lys Phe Arg Arg Pro Pro Leu Asp Gly Lys Cys Pro Ile Cys Gly
    1130                1135                1140

Gly Lys Ile Val Leu Thr Val Ser Lys Gly Ala Ile Glu Lys Tyr
    1145                1150                1155

Leu Gly Thr Ala Lys Met Leu Val Thr Glu Tyr Lys Val Lys Asn
    1160                1165                1170

Tyr Thr Arg Gln Arg Ile Cys Leu Thr Glu Arg Asp Ile Asp Ser
    1175                1180                1185

Leu Phe Glu Thr Val Phe Pro Glu Thr Gln Leu Thr Leu Leu Val
    1190                1195                1200

Asn Pro Asn Asp Ile Cys Gln Arg Ile Ile Met Glu Arg Thr Gly
    1205                1210                1215

Gly Ser Lys Lys Ser Gly Leu Leu Glu Asn Phe Ala Asn Gly Tyr
    1220                1225                1230

Asn Lys Gly Lys Lys Glu Glu Met Pro Lys Lys Gln Arg Lys Lys
    1235                1240                1245

Glu Gln Glu Lys Ser Lys Lys Arg Lys Val Ile Ser Leu Asp Asp
    1250                1255                1260

Phe Phe Ser Arg Lys
    1265
```

<210> SEQ ID NO 5
<211> LENGTH: 1869
<212> TYPE: DNA
<213> ORGANISM: Pyrococcus horikoshii
<220> FEATURE:
<223> OTHER INFORMATION: polD small subunit

<400> SEQUENCE: 5

| | | | | | | |
|---|---|---|---|---|---|---|
| atggatgaat | tcgtaaaggg | attaatgaaa | aacgggtacc | ttataactcc | ttctgcctat | 60 |
| tacctcttag | ttggccattt | caatgaggga | aagttctcgc | tcatagaatt | gataaaattt | 120 |
| gcaaaatcca | gggaaacgtt | catcatagat | gatgagattg | ctaatgaatt | ccttaagtcc | 180 |
| atcggggctg | aagttgaact | tccacaggaa | ataaggagg | gttacatttc | cactggagaa | 240 |
| ggttcacaga | aggttccaga | tcatgaagaa | ctggaaaaaa | taacgaatga | atctagtgta | 300 |
| gagagttcta | tttccactgg | agaaactcca | aaaactgagg | aactacagcc | tactttagat | 360 |
| atattagagg | aagaaatagg | ggacattgaa | ggtggagaga | gttctatttc | cactggagat | 420 |
| gaagtccccg | aagtggaaaa | taataatgga | ggtacggtgg | tagttttcga | taaatacggc | 480 |
| tatcccttca | cgtatgttcc | agaggaaatt | gaggaagaac | tagaagagta | tcctaagtat | 540 |
| gaagatgtaa | caattgagat | caatcctaac | ctcgaagtcg | ttccgataga | aaaagactat | 600 |
| gagataaaat | ttgacgttag | acgagtaaaa | cttaagcctc | caaaggttaa | gagcggttcg | 660 |
| ggaaaagagg | gagagataat | agttgaggct | tatgcctctc | ttttcaggag | taggttaagg | 720 |
| aagcttagaa | ggatcttaag | ggaaaatcct | gaagtgagca | atgttattga | tataaagaag | 780 |
| ctgaaatacg | tcaagggtga | tgaggaggtt | actataatag | ggctcgtcaa | tagtaagaag | 840 |
| gagacctcta | aggggctgat | atttgaggtc | gaggatcaaa | cggatagagt | taaggtgttt | 900 |
| cttccgaaag | actctgaaga | ttacaggaa | gccttgaaag | ttcttcccga | tgctgtagtt | 960 |
| gctttcaagg | gagtttattc | gaaaagggga | atattctttg | caaatagatt | ttatttacct | 1020 |
| gatgttccgc | tatatagaaa | gcagaagccc | ccattggaag | agaaggttta | cgccgttttg | 1080 |
| acgagtgata | tccacgttgg | aagcaaggaa | ttttgtgaaa | aggcatttat | taagttcctg | 1140 |
| gagtggctta | atggttacgt | tgagagcaag | gaggaagaag | agattgtaag | tagaataagg | 1200 |
| tatttaatta | tagcagggga | tgttgtcgat | ggcatcggaa | tttatcctgg | ccagtattct | 1260 |
| gacctaataa | ttcccgatat | ctttgatcag | tatgaggccc | ttgcgaacct | cctctcgaac | 1320 |
| gttcccaagc | atataacgat | cttcataggc | cccggtaatc | atgatgctgc | aaggcccgca | 1380 |
| ataccgcaac | ctgagttta | cgaggagtac | gcgaagcccc | tgtataagtt | gaagaatact | 1440 |
| gtgataatca | gcaacccagc | ggtcataagg | cttcatggta | gggattttt | gatagcccat | 1500 |
| ggaaggggaa | tagaggatgt | tgtttcattc | gttcctggat | tgacgcatca | taaacctggc | 1560 |
| ttacccatgg | ttgagttgct | taaaatgaga | catttagctc | caacctttgg | agggaaggtt | 1620 |
| ccgatcgctc | cagatcctga | ggatctattg | gtaatagagg | aagttccgga | tctagttcag | 1680 |
| atgggacatg | tgcatgttta | cgatactgcg | gtttataggg | gtgtgcaact | cgtgaactcg | 1740 |
| gcaacttggc | aagcacagac | tgaattccag | aagatggtta | acatagtccc | aaccccggg | 1800 |
| ttggtaccaa | tagttgatgt | cgaaagcgcg | agggttatta | aagttctcga | ctttagtagg | 1860 |
| tggtgctga | | | | | | 1869 |

<210> SEQ ID NO 6
<211> LENGTH: 622
<212> TYPE: PRT
<213> ORGANISM: Pyrococcus horikoshii
<220> FEATURE:

<223> OTHER INFORMATION: polD small subunit

<400> SEQUENCE: 6

```
Met Asp Glu Phe Val Lys Gly Leu Met Lys Asn Gly Tyr Leu Ile Thr
1               5                   10                  15

Pro Ser Ala Tyr Tyr Leu Leu Val Gly His Phe Asn Glu Gly Lys Phe
            20                  25                  30

Ser Leu Ile Glu Leu Ile Lys Phe Ala Lys Ser Arg Glu Thr Phe Ile
        35                  40                  45

Ile Asp Asp Glu Ile Ala Asn Glu Phe Leu Lys Ser Ile Gly Ala Glu
    50                  55                  60

Val Glu Leu Pro Gln Glu Ile Lys Glu Gly Tyr Ile Ser Thr Gly Glu
65                  70                  75                  80

Gly Ser Gln Lys Val Pro Asp His Glu Leu Glu Lys Ile Thr Asn
                85                  90                  95

Glu Ser Ser Val Glu Ser Ser Ile Ser Thr Gly Glu Thr Pro Lys Thr
                100                 105                 110

Glu Glu Leu Gln Pro Thr Leu Asp Ile Leu Glu Glu Ile Gly Asp
            115                 120                 125

Ile Glu Gly Gly Glu Ser Ser Ile Ser Thr Gly Asp Glu Val Pro Glu
    130                 135                 140

Val Glu Asn Asn Asn Gly Gly Thr Val Val Phe Asp Lys Tyr Gly
145                 150                 155                 160

Tyr Pro Phe Thr Tyr Val Pro Glu Glu Ile Glu Glu Leu Glu Glu
                165                 170                 175

Tyr Pro Lys Tyr Glu Asp Val Thr Ile Glu Ile Asn Pro Asn Leu Glu
            180                 185                 190

Val Val Pro Ile Glu Lys Asp Tyr Glu Ile Lys Phe Asp Val Arg Arg
        195                 200                 205

Val Lys Leu Lys Pro Pro Lys Val Lys Ser Gly Ser Gly Lys Glu Gly
    210                 215                 220

Glu Ile Ile Val Glu Ala Tyr Ala Ser Leu Phe Arg Ser Arg Leu Arg
225                 230                 235                 240

Lys Leu Arg Arg Ile Leu Arg Glu Asn Pro Glu Val Ser Asn Val Ile
                245                 250                 255

Asp Ile Lys Lys Leu Lys Tyr Val Lys Gly Asp Glu Glu Val Thr Ile
            260                 265                 270

Ile Gly Leu Val Asn Ser Lys Lys Glu Thr Ser Lys Gly Leu Ile Phe
        275                 280                 285

Glu Val Glu Asp Gln Thr Asp Arg Val Lys Val Phe Leu Pro Lys Asp
    290                 295                 300

Ser Glu Asp Tyr Arg Glu Ala Leu Lys Val Leu Pro Asp Ala Val Val
305                 310                 315                 320

Ala Phe Lys Gly Val Tyr Ser Arg Gly Ile Phe Phe Ala Asn Arg
                325                 330                 335

Phe Tyr Leu Pro Asp Val Pro Leu Tyr Arg Lys Gln Lys Pro Pro Leu
            340                 345                 350

Glu Glu Lys Val Tyr Ala Val Leu Thr Ser Asp Ile His Val Gly Ser
        355                 360                 365

Lys Glu Phe Cys Glu Lys Ala Phe Ile Lys Phe Leu Glu Trp Leu Asn
    370                 375                 380

Gly Tyr Val Glu Ser Lys Glu Glu Glu Ile Val Ser Arg Ile Arg
385                 390                 395                 400
```

```
Tyr Leu Ile Ile Ala Gly Asp Val Val Asp Gly Ile Tyr Pro
                405                 410                 415
Gly Gln Tyr Ser Asp Leu Ile Ile Pro Asp Ile Phe Asp Gln Tyr Glu
            420                 425                 430
Ala Leu Ala Asn Leu Leu Ser Asn Val Pro Lys His Ile Thr Ile Phe
            435                 440                 445
Ile Gly Pro Gly Asn His Asp Ala Ala Arg Pro Ala Ile Pro Gln Pro
        450                 455                 460
Glu Phe Tyr Glu Glu Tyr Ala Lys Pro Leu Tyr Lys Leu Lys Asn Thr
465                 470                 475                 480
Val Ile Ile Ser Asn Pro Ala Val Ile Arg Leu His Gly Arg Asp Phe
                485                 490                 495
Leu Ile Ala His Gly Arg Gly Ile Glu Asp Val Val Ser Phe Val Pro
            500                 505                 510
Gly Leu Thr His His Lys Pro Gly Leu Pro Met Val Glu Leu Leu Lys
            515                 520                 525
Met Arg His Leu Ala Pro Thr Phe Gly Gly Lys Val Pro Ile Ala Pro
        530                 535                 540
Asp Pro Glu Asp Leu Leu Val Ile Glu Glu Val Pro Asp Leu Val Gln
545                 550                 555                 560
Met Gly His Val His Val Tyr Asp Thr Ala Val Tyr Arg Gly Val Gln
                565                 570                 575
Leu Val Asn Ser Ala Thr Trp Gln Ala Gln Thr Glu Phe Gln Lys Met
            580                 585                 590
Val Asn Ile Val Pro Thr Pro Gly Leu Val Pro Ile Val Asp Val Glu
        595                 600                 605
Ser Ala Arg Val Ile Lys Val Leu Asp Phe Ser Arg Trp Cys
    610                 615                 620

<210> SEQ ID NO 7
<211> LENGTH: 750
<212> TYPE: DNA
<213> ORGANISM: Pyrococcus horikoshii
<220> FEATURE:
<223> OTHER INFORMATION: PCNA

<400> SEQUENCE: 7
atgccattcg aaatagtctt tgagggtgca aaggaatttg cccagctcat agagacggcc      60
agcaggctta tagatgaagc ggcctttaag gtaacagaag aaggaatatc aatgagggct     120
atggatccga gtagagtagt tttaattgac cttaacttac cttcgagcat attcagtaag     180
tatgaggtgg atggggaaga gacgataggt gtcaatatgg atcacctaaa gaaagttctt     240
aagagaggta aggccaagga tacgcttatc ttgagaaaag gagaagagaa cttcctagaa     300
ataagcctcc aagggactgc tactagaacc tttagattac ccctaatcga cgttgaagag     360
atcgaagtgg aattacctga tctcccgtat acagcaaagg ttgtcgttct gggcgaagtg     420
cttaaggaag cagttaaaga tgcttcctta gtaagcgata gcataaagtt catggctaag     480
gaaaatgagt ttatcatgag agcggaagga gaaacccagg aagttgaagt taagttaacc     540
ctggaggatg agggttact  tgatatagaa gttcaagagg agacaaagag cgcttatggg     600
gttagttatc tagcggatat ggtaaaggga ataggaaagg ccgatgaagt gacaatgaga     660
ttcgggaatg aaatgccgat gcagatggag tactatatta gggatgaagg taggttaacg     720
ttcctgctag ccccaagggt tgaggagtga                                     750
```

<210> SEQ ID NO 8
<211> LENGTH: 249
<212> TYPE: PRT
<213> ORGANISM: Pyrococcus horikoshii
<220> FEATURE:
<223> OTHER INFORMATION: PCNA

<400> SEQUENCE: 8

Met Pro Phe Glu Ile Val Phe Glu Gly Ala Lys Glu Phe Ala Gln Leu
1               5                   10                  15

Ile Glu Thr Ala Ser Arg Leu Ile Asp Glu Ala Ala Phe Lys Val Thr
            20                  25                  30

Glu Glu Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Asp
50                  55                  60

Gly Glu Glu Thr Ile Gly Val Asn Met Asp His Leu Lys Lys Val Leu
65                  70                  75                  80

Lys Arg Gly Lys Ala Lys Asp Thr Leu Ile Leu Arg Lys Gly Glu Glu
                85                  90                  95

Asn Phe Leu Glu Ile Ser Leu Gln Gly Thr Ala Thr Arg Thr Phe Arg
            100                 105                 110

Leu Pro Leu Ile Asp Val Glu Glu Ile Glu Val Glu Leu Pro Asp Leu
        115                 120                 125

Pro Tyr Thr Ala Lys Val Val Val Leu Gly Glu Val Leu Lys Glu Ala
130                 135                 140

Val Lys Asp Ala Ser Leu Val Ser Asp Ser Ile Lys Phe Met Ala Lys
145                 150                 155                 160

Glu Asn Glu Phe Ile Met Arg Ala Glu Gly Glu Thr Gln Glu Val Glu
                165                 170                 175

Val Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ala Asp Met Val
        195                 200                 205

Lys Gly Ile Gly Lys Ala Asp Glu Val Thr Met Arg Phe Gly Asn Glu
210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245

<210> SEQ ID NO 9
<211> LENGTH: 1407
<212> TYPE: DNA
<213> ORGANISM: Pyrococcus horikoshii
<220> FEATURE:
<223> OTHER INFORMATION: RFC large subunit

<400> SEQUENCE: 9
atgcccgatg ttccatggat tgagaagtac aggccaagga agttaagtga aatagttaac      60
caagagcagg ccctagagaa agttagagca tggatagaat cctggttaca tggaaatcca     120
ccgaagaaaa aagccttatt attggccggg cccccaggaa gtgggaagac taccacggtt     180
tacgccctag ctcacgaata caactttgag gttatagagc tcaatgctag cgacgagagg     240
acttataaca agatagctag gtacgttcaa gcggcctata caatggatat catgggtaag     300
aggaggaaga taatcttcct ggatgaagcc gacaatattg aacctagtgg agctccggaa     360

```
attgcaaagc taatagataa ggccaggaac cccataataa tggccgcaaa tcactactgg    420
gaagttccaa aggaaataag agatagagct gagctcgttg agtataagag attaaaccag    480
agggatgtta tctctgcttt agtcagaata ctcaagagag aaggaataac agtccccaag    540
gagatcctca cggaaatagc gaagagatca agcggtgatc tgagagctgc gataaacgac    600
cttcaaacga ttgtggccgg tggatatgag gatgcaaagt atgtcttagc ttacagagac    660
gttgaaaaga cggtattcca atctctcggg atggtattta gtagtgataa tgctaagagg    720
gcaaagctag ccctaatgaa cctggatatg tccccagatg agttcctatt atgggtcgat    780
gagaacatac ctcacatgta ccttaagccc gaggaaatgg cgagggctta tgaagcgata    840
agtagagctg atatctacct aggaagggct cagagaacgg gaaattactc gctttggaag    900
tacgccatag acatgatgac cgctggagtt gccgtggcgg gaactaaaaa gaagggattt    960
gcaaagtttt atcccccaaa taccctaaaa atgctcgcag agagcaaaga ggagagatcc   1020
ataagggatt ccattattaa gaaaataatg aaagagatgc acatgagcaa gcttgaagcc   1080
ctggaaacta tgaaaatcct caggacgata ttcgagaaca acctagatct tgcagctcat   1140
ttcacggtct ttttagagct tacggagaag gaagttgagt tcctagcagg aaaggaaaag   1200
gccggaacga tctggggtaa aacactttcc ataaggagaa ggattaagga aacagaaaaa   1260
attgaagaga aagccgttga ggagaaagta gaggaggaag aagctgaaga ggaagaagag   1320
gaggagagga aggaagagga aagcccaaaa gctgaaaaga gaaagggaa gcaggtcaca   1380 ctctttgact ttattaagaa gaattag                                        1407

<210> SEQ ID NO 10
<211> LENGTH: 468
<212> TYPE: PRT
<213> ORGANISM: Pyrococcus horikoshii
<220> FEATURE:
<223> OTHER INFORMATION: RFC large subunit

<400> SEQUENCE: 10

Met Pro Asp Val Pro Trp Ile Glu Lys Tyr Arg Pro Arg Lys Leu Ser
1               5                  10                  15

Glu Ile Val Asn Gln Glu Gln Ala Leu Glu Lys Val Arg Ala Trp Ile
                20                  25                  30

Glu Ser Trp Leu His Gly Asn Pro Pro Lys Lys Ala Leu Leu Leu
            35                  40                  45

Ala Gly Pro Pro Gly Ser Gly Lys Thr Thr Thr Val Tyr Ala Leu Ala
        50                  55                  60

His Glu Tyr Asn Phe Glu Val Ile Glu Leu Asn Ala Ser Asp Glu Arg
65                  70                  75                  80

Thr Tyr Asn Lys Ile Ala Arg Tyr Val Gln Ala Ala Tyr Thr Met Asp
                85                  90                  95

Ile Met Gly Lys Arg Arg Lys Ile Ile Phe Leu Asp Glu Ala Asp Asn
            100                 105                 110

Ile Glu Pro Ser Gly Ala Pro Glu Ile Ala Lys Leu Ile Asp Lys Ala
        115                 120                 125

Arg Asn Pro Ile Ile Met Ala Ala Asn His Tyr Trp Glu Val Pro Lys
    130                 135                 140

Glu Ile Arg Asp Arg Ala Glu Leu Val Glu Tyr Lys Arg Leu Asn Gln
145                 150                 155                 160

Arg Asp Val Ile Ser Ala Leu Val Arg Ile Leu Lys Arg Glu Gly Ile
                165                 170                 175
```

```
Thr Val Pro Lys Glu Ile Leu Thr Glu Ile Ala Lys Arg Ser Ser Gly
            180                 185                 190

Asp Leu Arg Ala Ala Ile Asn Asp Leu Gln Thr Ile Val Ala Gly Gly
            195                 200                 205

Tyr Glu Asp Ala Lys Tyr Val Leu Ala Tyr Arg Asp Val Glu Lys Thr
            210                 215                 220

Val Phe Gln Ser Leu Gly Met Val Phe Ser Ser Asp Asn Ala Lys Arg
225                 230                 235                 240

Ala Lys Leu Ala Leu Met Asn Leu Asp Met Ser Pro Asp Glu Phe Leu
            245                 250                 255

Leu Trp Val Asp Glu Asn Ile Pro His Met Tyr Leu Lys Pro Glu Glu
            260                 265                 270

Met Ala Arg Ala Tyr Glu Ala Ile Ser Arg Ala Asp Ile Tyr Leu Gly
            275                 280                 285

Arg Ala Gln Arg Thr Gly Asn Tyr Ser Leu Trp Lys Tyr Ala Ile Asp
            290                 295                 300

Met Met Thr Ala Gly Val Ala Val Ala Gly Thr Lys Lys Lys Gly Phe
305                 310                 315                 320

Ala Lys Phe Tyr Pro Pro Asn Thr Leu Lys Met Leu Ala Glu Ser Lys
            325                 330                 335

Glu Glu Arg Ser Ile Arg Asp Ser Ile Ile Lys Lys Ile Met Lys Glu
            340                 345                 350

Met His Met Ser Lys Leu Glu Ala Leu Glu Thr Met Lys Ile Leu Arg
            355                 360                 365

Thr Ile Phe Glu Asn Asn Leu Asp Leu Ala Ala His Phe Thr Val Phe
            370                 375                 380

Leu Glu Leu Thr Glu Lys Glu Val Glu Phe Leu Ala Gly Lys Glu Lys
385                 390                 395                 400

Ala Gly Thr Ile Trp Gly Lys Thr Leu Ser Ile Arg Arg Ile Lys
            405                 410                 415

Glu Thr Glu Lys Ile Glu Glu Lys Ala Val Glu Lys Val Glu Glu
            420                 425                 430

Glu Glu Ala Glu Glu Glu Glu Glu Glu Arg Lys Glu Glu Glu Lys
            435                 440                 445

Pro Lys Ala Glu Lys Lys Lys Gly Lys Gln Val Thr Leu Phe Asp Phe
450                 455                 460

Ile Lys Lys Asn
465

<210> SEQ ID NO 11
<211> LENGTH: 2568
<212> TYPE: DNA
<213> ORGANISM: Pyrococcus horikoshii
<220> FEATURE:
<223> OTHER INFORMATION: RFC small subunit(+intein)

<400> SEQUENCE: 11
gtgcataata tggaagaggt tagagaggta aaggttcttg aaaaaccatg ggttgaaaag      60
tataggcctc agagattaga tgagatagtg ggtcaagagc atatagttaa gaggcttaaa     120
cactacgtta aaactgggtc aatgccccat ttactatttg caggtcctcc tggtgttgga     180
aagtgcctca ccggagatac taaagttata gctaacggtc aactcttcga acttagggag     240
cttgtcgaaa aaatctccgg aggaaaattc ggcccaactc ccgttaaggg gttaaaagtt     300
attgggatag atgaagatgg aaagcttaga gagttcgaag ttcaatatgt ttacaaagat     360
```

```
aaaactgaga ggctaataag gataaggact cgccttggaa gggagcttaa ggtaacccca    420
taccatcccc tcctcgtgaa tagaaggaac ggagagataa agtgggttaa agccgaagaa    480
ctcaaacctg gtgacaaact tgcggtaccg cgtttcttac ccattgtaac cggagaagat    540
cctctggcag agtggcttgg ctacttcctc ggaggcggtt atgctgactc aaaggagaac    600
ttaatcatgt ttaccaatga agatcccctc ctaagacaac gcttcatgga gctaacggaa    660
aagcttttct cagatgcaag gataagggag ataacccacg agaatggaac ttcaaaagtt    720
tatgtaaact ccaagaaagc cttaaagcta gtaaactccc taggaaatgc tcacataccc    780
aaagaatgct ggagaggaat tcggtctttc ctcagggctt acttcgactg caatggtggc    840
gtcaagggga acgctatagt cctagcaaca gctagcaagg agatgtccca ggaaatagca    900
tatgctctag ccggctttgg aataatctca aggatacaag aataccgcgt tattatatca    960
ggctcagata acgtaaagaa gttcctaaat gagatcggct ttattaatcg gaataaactt   1020
gaaaaggccc taaagcttgt taaaaaagat gatccaggtc atgatggctt ggagatcaac   1080
tatgagctaa tatcctacgt taaagatagg cttaggttaa gtttctttaa cgataagaga   1140
agttggagct acagagaagc gaaggaaatt tcctgggagc tgatgaaaga gatctactac   1200
cgccttgatg agcttgagaa gctgaaagag tctttgtcaa ggggtatcct aatcgactgg   1260
aacgaagtag caaagaggat agaagaggta gcagaagaaa ctggaattag agcagatgaa   1320
ctccttgagt acatagaagg aaaaagaaag ctgagtttca aggattacat aaagatagca   1380
aaggttcttg gaattgacgt tgaacatacc atcgaagcta tgagagtttt tgcaagaaag   1440
tattcaagct acgctgagat tggaaggaga ctcggtacct ggaattctag cgtgaagaca   1500
attctcgaga gcaacgccgt gaacgttgaa atcctagaga ggataaggaa aattgaactt   1560
gaactcatag aggaaatact ctccgatgaa aagctcaagg aagggatagc gtacttaatc   1620
ttcctctcgc aaaatgagct ttattgggat gagataacta agtagaaga gcttagggga   1680
gagttcataa tctacgatct tcacgttcct gggtaccaca acttcatagc tggaaacatg   1740
ccaacggtag ttcacaatac tacagcagct ttagccctct caagagagct tttcggcgag   1800
aactggaggc ataatttcct tgaattgaat gcttcagatg agagaggtat aaacgtgatt   1860
agagagaaag ttaaggagtt tgcaaggaca aaacccatag gaggagcgag cttcaagata   1920
atcttccttg acgaggccga cgctttaact caagatgccc agcaagcatt aaggagaacc   1980
atggagatgt tctcgagcaa cgttcgcttt atcttaagct gtaactactc ctcaaagatc   2040
attgagccca tacagtctag atgtgcgata ttccgcttca gaccccctccg tgatgaggac   2100
atagcaaaga gattaaggta cattgccgaa aatgaaggtt tagagctaac tgaagaaggt   2160
ctccaagcaa tactttacat agccgaagga gacatgagaa gggccataaa cattctgcaa   2220
gctgcagcgg ccctggacaa gaaaattacc gatgaaaatg tattcatggt agcgagtagg   2280
gctagaccaa aggatataag ggagatgatg ctcttagccc ttaagggtaa cttcctgaag   2340
gctagagaaa agctcaggga aatactcctc aagcaggggc ttagtggaga ggatgtctta   2400
attcagatgc acaaagaggt atttaactta ccgatagatg agcccactaa agtttaccta   2460
gcggataaga taggagagta caacttcagg ctcgttgaag gagctaacga gatgatacag   2520
cttgaagccc tcttagctca atttacctta gttggaaaga agaagtga                2568
```

<210> SEQ ID NO 12  
<211> LENGTH: 855  
<212> TYPE: PRT  
<213> ORGANISM: Pyrococcus horikoshii
<220> FEATURE:
<223> OTHER INFORMATION: RFC small subunit(+intein)

<400> SEQUENCE: 12

```
Met His Asn Met Glu Glu Val Arg Glu Val Lys Val Leu Glu Lys Pro
1               5                   10                  15

Trp Val Glu Lys Tyr Arg Pro Gln Arg Leu Asp Glu Ile Val Gly Gln
            20                  25                  30

Glu His Ile Val Lys Arg Leu His Tyr Val Lys Thr Gly Ser Met
        35                  40                  45

Pro His Leu Leu Phe Ala Gly Pro Pro Gly Val Gly Lys Cys Leu Thr
    50                  55                  60

Gly Asp Thr Lys Val Ile Ala Asn Gly Gln Leu Phe Glu Leu Arg Glu
65                  70                  75                  80

Leu Val Glu Lys Ile Ser Gly Gly Lys Phe Gly Pro Thr Pro Val Lys
                85                  90                  95

Gly Leu Lys Val Ile Gly Ile Asp Glu Asp Gly Lys Leu Arg Glu Phe
            100                 105                 110

Glu Val Gln Tyr Val Tyr Lys Asp Lys Thr Glu Arg Leu Ile Arg Ile
        115                 120                 125

Arg Thr Arg Leu Gly Arg Glu Leu Lys Val Thr Pro Tyr His Pro Leu
130                 135                 140

Leu Val Asn Arg Arg Asn Gly Glu Ile Lys Trp Val Lys Ala Glu Glu
145                 150                 155                 160

Leu Lys Pro Gly Asp Lys Leu Ala Val Pro Arg Phe Leu Pro Ile Val
                165                 170                 175

Thr Gly Glu Asp Pro Leu Ala Glu Trp Leu Gly Tyr Phe Leu Gly Gly
            180                 185                 190

Gly Tyr Ala Asp Ser Lys Glu Asn Leu Ile Met Phe Thr Asn Glu Asp
        195                 200                 205

Pro Leu Leu Arg Gln Arg Phe Met Glu Leu Thr Glu Lys Leu Phe Ser
    210                 215                 220

Asp Ala Arg Ile Arg Glu Ile Thr His Glu Asn Gly Thr Ser Lys Val
225                 230                 235                 240

Tyr Val Asn Ser Lys Lys Ala Leu Lys Leu Val Asn Ser Leu Gly Asn
                245                 250                 255

Ala His Ile Pro Lys Glu Cys Trp Arg Gly Ile Arg Ser Phe Leu Arg
            260                 265                 270

Ala Tyr Phe Asp Cys Asn Gly Gly Val Lys Gly Asn Ala Ile Val Leu
        275                 280                 285

Ala Thr Ala Ser Lys Glu Met Ser Gln Glu Ile Ala Tyr Ala Leu Ala
    290                 295                 300

Gly Phe Gly Ile Ile Ser Arg Ile Gln Glu Tyr Arg Val Ile Ile Ser
305                 310                 315                 320

Gly Ser Asp Asn Val Lys Lys Phe Leu Asn Glu Ile Gly Phe Ile Asn
                325                 330                 335

Arg Asn Lys Leu Glu Lys Ala Leu Lys Leu Val Lys Lys Asp Asp Pro
            340                 345                 350

Gly His Asp Gly Leu Glu Ile Asn Tyr Glu Leu Ile Ser Tyr Val Lys
        355                 360                 365

Asp Arg Leu Arg Leu Ser Phe Phe Asn Asp Lys Arg Ser Trp Ser Tyr
    370                 375                 380

Arg Glu Ala Lys Glu Ile Ser Trp Glu Leu Met Lys Glu Ile Tyr Tyr
385                 390                 395                 400
```

-continued

```
Arg Leu Asp Glu Leu Glu Lys Leu Lys Glu Ser Leu Ser Arg Gly Ile
            405                 410                 415
Leu Ile Asp Trp Asn Glu Val Ala Lys Arg Ile Glu Glu Val Ala Glu
        420                 425                 430
Glu Thr Gly Ile Arg Ala Asp Glu Leu Leu Glu Tyr Ile Glu Gly Lys
    435                 440                 445
Arg Lys Leu Ser Phe Lys Asp Tyr Ile Lys Ile Ala Lys Val Leu Gly
450                 455                 460
Ile Asp Val Glu His Thr Ile Glu Ala Met Arg Val Phe Ala Arg Lys
465                 470                 475                 480
Tyr Ser Ser Tyr Ala Glu Ile Gly Arg Arg Leu Gly Thr Trp Asn Ser
                485                 490                 495
Ser Val Lys Thr Ile Leu Glu Ser Asn Ala Val Asn Val Glu Ile Leu
            500                 505                 510
Glu Arg Ile Arg Lys Ile Glu Leu Glu Leu Ile Glu Glu Ile Leu Ser
        515                 520                 525
Asp Glu Lys Leu Lys Glu Gly Ile Ala Tyr Leu Ile Phe Leu Ser Gln
    530                 535                 540
Asn Glu Leu Tyr Trp Asp Glu Ile Thr Lys Val Glu Glu Leu Arg Gly
545                 550                 555                 560
Glu Phe Ile Ile Tyr Asp Leu His Val Pro Gly Tyr His Asn Phe Ile
                565                 570                 575
Ala Gly Asn Met Pro Thr Val Val His Asn Thr Thr Ala Ala Leu Ala
            580                 585                 590
Leu Ser Arg Glu Leu Phe Gly Glu Asn Trp Arg His Asn Phe Leu Glu
        595                 600                 605
Leu Asn Ala Ser Asp Glu Arg Gly Ile Asn Val Ile Arg Glu Lys Val
    610                 615                 620
Lys Glu Phe Ala Arg Thr Lys Pro Ile Gly Gly Ala Ser Phe Lys Ile
625                 630                 635                 640
Ile Phe Leu Asp Glu Ala Asp Ala Leu Thr Gln Asp Ala Gln Gln Ala
                645                 650                 655
Leu Arg Arg Thr Met Glu Met Phe Ser Ser Asn Val Arg Phe Ile Leu
            660                 665                 670
Ser Cys Asn Tyr Ser Ser Lys Ile Ile Glu Pro Ile Gln Ser Arg Cys
        675                 680                 685
Ala Ile Phe Arg Phe Arg Pro Leu Arg Asp Glu Asp Ile Ala Lys Arg
    690                 695                 700
Leu Arg Tyr Ile Ala Glu Asn Glu Gly Leu Glu Leu Thr Glu Glu Gly
705                 710                 715                 720
Leu Gln Ala Ile Leu Tyr Ile Ala Glu Gly Asp Met Arg Arg Ala Ile
                725                 730                 735
Asn Ile Leu Gln Ala Ala Ala Leu Asp Lys Lys Ile Thr Asp Glu
            740                 745                 750
Asn Val Phe Met Val Ala Ser Arg Ala Arg Pro Glu Asp Ile Arg Glu
        755                 760                 765
Met Met Leu Leu Ala Leu Lys Gly Asn Phe Leu Lys Ala Arg Glu Lys
    770                 775                 780
Leu Arg Glu Ile Leu Leu Lys Gln Gly Leu Ser Gly Glu Asp Val Leu
785                 790                 795                 800
Ile Gln Met His Lys Glu Val Phe Asn Leu Pro Ile Asp Glu Pro Thr
                805                 810                 815
```

```
Lys Val Tyr Leu Ala Asp Lys Ile Gly Glu Tyr Asn Phe Arg Leu Val
            820                 825                 830

Glu Gly Ala Asn Glu Met Ile Gln Leu Glu Ala Leu Leu Ala Gln Phe
            835                 840                 845

Thr Leu Val Gly Lys Lys Lys
            850         855
```

<210> SEQ ID NO 13
<211> LENGTH: 993
<212> TYPE: DNA
<213> ORGANISM: Pyrococcus horikoshii
<220> FEATURE:
<223> OTHER INFORMATION: RFC small subunit(-intein)

<400> SEQUENCE: 13

```
gtgcataata tggaagaggt tagagaggta aaggttcttg aaaaaccatg ggttgaaaag      60
tataggcctc agagattaga tgagatagtg ggtcaagagc atatagttaa gaggcttaaa     120
cactacgtta aaactgggtc aatgccccat ttactatttg caggtcctcc tggtgttgga     180
aagactacag cagctttagc cctctcaaga gagcttttcg gcgagaactg gaggcataat     240
ttccttgaat tgaatgcttc agatgagaga ggtataaacg tgattagaga aaagttaag     300
gagtttgcaa ggacaaaacc cataggagga gcgagcttca agataatctt ccttgacgag     360
gccgacgctt taactcaaga tgcccagcaa gcattaagga gaaccatgga gatgttctcg     420
agcaacgttc gctttatctt aagctgtaac tactcctcaa agatcattga gcccatacag     480
tctagatgtg cgatattccg cttcagaccc ctccgtgatg aggacatagc aaagagatta     540
aggtacattg ccgaaaatga aggtttagag ctaactgaag aaggtctcca agcaatactt     600
tacatagccg aaggagacat gagaagggcc ataaacattc tgcaagctgc agcggccctg     660
gacaagaaaa ttaccgatga aaatgtattc atggtagcga gtagggctag accagaggat     720
ataagggaga tgatgctctt agcccttaag ggtaacttcc tgaaggctag agaaaagctc     780
agggaaatac tcctcaagca ggggcttagt ggagaggatg tcttaattca gatgcacaaa     840
gaggtattta acttaccgat agatgagccc actaaagttt acctagcgga taagatagga     900
gagtacaact tcaggctcgt tgaaggagct aacgagatga tacagcttga agccctctta     960
gctcaattta ccttagttgg aaagaagaag tga                                  993
```

<210> SEQ ID NO 14
<211> LENGTH: 330
<212> TYPE: PRT
<213> ORGANISM: Pyrococcus horikoshii
<220> FEATURE:
<223> OTHER INFORMATION: RFC small subunit(-intein)

<400> SEQUENCE: 14

```
Met His Asn Met Glu Glu Val Arg Glu Val Lys Val Leu Glu Lys Pro
1               5                   10                  15

Trp Val Glu Lys Tyr Arg Pro Gln Arg Leu Asp Glu Ile Val Gly Gln
            20                  25                  30

Glu His Ile Val Lys Arg Leu Lys His Tyr Val Lys Thr Gly Ser Met
        35                  40                  45

Pro His Leu Leu Phe Ala Gly Pro Pro Gly Val Gly Lys Thr Thr Ala
    50                  55                  60

Ala Leu Ala Leu Ser Arg Glu Leu Phe Gly Glu Asn Trp Arg His Asn
65                  70                  75                  80

Phe Leu Glu Leu Asn Ala Ser Asp Glu Arg Gly Ile Asn Val Ile Arg
```

-continued

```
                     85                  90                  95
Glu Lys Val Lys Glu Phe Ala Arg Thr Lys Pro Ile Gly Gly Ala Ser
                100                 105                 110
Phe Lys Ile Ile Phe Leu Asp Glu Ala Asp Ala Leu Thr Gln Asp Ala
                115                 120                 125
Gln Gln Ala Leu Arg Arg Thr Met Glu Met Phe Ser Ser Asn Val Arg
                130                 135                 140
Phe Ile Leu Ser Cys Asn Tyr Ser Ser Lys Ile Ile Glu Pro Ile Gln
145                 150                 155                 160
Ser Arg Cys Ala Ile Phe Arg Phe Arg Pro Leu Arg Asp Glu Asp Ile
                165                 170                 175
Ala Lys Arg Leu Arg Tyr Ile Ala Glu Asn Glu Gly Leu Glu Leu Thr
                180                 185                 190
Glu Glu Gly Leu Gln Ala Ile Leu Tyr Ile Ala Glu Gly Asp Met Arg
                195                 200                 205
Arg Ala Ile Asn Ile Leu Gln Ala Ala Ala Leu Asp Lys Lys Ile
                210                 215                 220
Thr Asp Glu Asn Val Phe Met Val Ala Ser Arg Ala Arg Pro Glu Asp
225                 230                 235                 240
Ile Arg Glu Met Met Leu Leu Ala Leu Lys Gly Asn Phe Leu Lys Ala
                245                 250                 255
Arg Glu Lys Leu Arg Glu Ile Leu Leu Lys Gln Gly Leu Ser Gly Glu
                260                 265                 270
Asp Val Leu Ile Gln Met His Lys Glu Val Phe Asn Leu Pro Ile Asp
                275                 280                 285
Glu Pro Thr Lys Val Tyr Leu Ala Asp Lys Ile Gly Glu Tyr Asn Phe
                290                 295                 300
Arg Leu Val Glu Gly Ala Asn Glu Met Ile Gln Leu Glu Ala Leu Leu
305                 310                 315                 320
Ala Gln Phe Thr Leu Val Gly Lys Lys Lys
                325                 330

<210> SEQ ID NO 15
<211> LENGTH: 34
<212> TYPE: DNA
<213> ORGANISM: Artificial
<220> FEATURE:
<223> OTHER INFORMATION: Primer

<400> SEQUENCE: 15
ttttgtcgac gtacatatgg atgaattcgt aaag                              34

<210> SEQ ID NO 16
<211> LENGTH: 43
<212> TYPE: DNA
<213> ORGANISM: Artificial
<220> FEATURE:
<223> OTHER INFORMATION: Primer

<400> SEQUENCE: 16
ttttgagctc tttggatcct tagaagctcc atcagcacca cct                    43

<210> SEQ ID NO 17
<211> LENGTH: 30
<212> TYPE: DNA
<213> ORGANISM: Artificial
<220> FEATURE:
<223> OTHER INFORMATION: Primer
```

```
<400> SEQUENCE: 17 ctcgactttα gcatatggct ctgatggagc                                       30

<210> SEQ ID NO 18
<211> LENGTH: 50
<212> TYPE: DNA
<213> ORGANISM: Artificial
<220> FEATURE:
<223> OTHER INFORMATION: Primer

<400> SEQUENCE: 18
gcttgtcgac gccataaact ttgacattat ccattgcgcg cttaagcaac                  50

<210> SEQ ID NO 19
<211> LENGTH: 24
<212> TYPE: DNA
<213> ORGANISM: Artificial
<220> FEATURE:
<223> OTHER INFORMATION: Primer

<400> SEQUENCE: 19
tttatggcgt cgacaagctg aagg                                             24

<210> SEQ ID NO 20
<211> LENGTH: 35
<212> TYPE: DNA
<213> ORGANISM: Artificial
<220> FEATURE:
<223> OTHER INFORMATION: Primer

<400> SEQUENCE: 20
tataacttat gcattgtggt tatttcgctg agaag                                 35

<210> SEQ ID NO 21
<211> LENGTH: 42
<212> TYPE: DNA
<213> ORGANISM: Artificial
<220> FEATURE:
<223> OTHER INFORMATION: Primer

<400> SEQUENCE: 21
cacgctgcaa agaggagaaa ttgcgatggt gatgaagatg ct                         42

<210> SEQ ID NO 22
<211> LENGTH: 42
<212> TYPE: DNA
<213> ORGANISM: Artificial
<220> FEATURE:
<223> OTHER INFORMATION: Primer

<400> SEQUENCE: 22
agcatcttca tcaccatcgc aatttctcct ctttgcagcg tg                         42

<210> SEQ ID NO 23
<211> LENGTH: 52
<212> TYPE: DNA
<213> ORGANISM: Artificial
<220> FEATURE:
<223> OTHER INFORMATION: Primer

<400> SEQUENCE: 23
cgggatccat gcatggtcga caccgcggtc agcaccacct actaaagtcg ag              52

<210> SEQ ID NO 24
<211> LENGTH: 30
```

```
<212> TYPE: DNA
<213> ORGANISM: Artificial
<220> FEATURE:
<223> OTHER INFORMATION: Primer

<400> SEQUENCE: 24
ggtgtccgcg gctcactata gggagaccac                              30

<210> SEQ ID NO 25
<211> LENGTH: 34
<212> TYPE: DNA
<213> ORGANISM: Artificial
<220> FEATURE:
<223> OTHER INFORMATION: Primer

<400> SEQUENCE: 25
gggggcatat gccattcgaa atagtctttg aggg                         34

<210> SEQ ID NO 26
<211> LENGTH: 29
<212> TYPE: DNA
<213> ORGANISM: Artificial
<220> FEATURE:
<223> OTHER INFORMATION: Primer

<400> SEQUENCE: 26
gggggctcga gtcactcctc aacccttgg                               29

<210> SEQ ID NO 27
<211> LENGTH: 37
<212> TYPE: DNA
<213> ORGANISM: Artificial
<220> FEATURE:
<223> OTHER INFORMATION: Primer

<400> SEQUENCE: 27 gggggggcata tgcataatat ggaagaggtt cgcgagg                     37

<210> SEQ ID NO 28
<211> LENGTH: 36
<212> TYPE: DNA
<213> ORGANISM: Artificial
<220> FEATURE:
<223> OTHER INFORMATION: Primer

<400> SEQUENCE: 28
gggggatcct cacttcttct ttccaactaa ggtaaa                       36

<210> SEQ ID NO 29
<211> LENGTH: 48
<212> TYPE: DNA
<213> ORGANISM: Artificial
<220> FEATURE:
<223> OTHER INFORMATION: Primer

<400> SEQUENCE: 29
gcaggtcctc ctggtgttgg aaagactaca gcagctttag ccctctca          48

<210> SEQ ID NO 30
<211> LENGTH: 48
<212> TYPE: DNA
<213> ORGANISM: Artificial
<220> FEATURE:
<223> OTHER INFORMATION: Primer

<400> SEQUENCE: 30
```
tgagagggct aaagctgctg tagtctttcc aacaccagga ggacctgc            48

<210> SEQ ID NO 31
<211> LENGTH: 33
<212> TYPE: DNA
<213> ORGANISM: Artificial
<220> FEATURE:
<223> OTHER INFORMATION: Primer

<400> SEQUENCE: 31 gggggcata tgccggatgt tccatggatt gag                             33

<210> SEQ ID NO 32
<211> LENGTH: 60
<212> TYPE: DNA
<213> ORGANISM: Artificial
<220> FEATURE:
<223> OTHER INFORMATION: Primer

<400> SEQUENCE: 32
gggggatccg gggatgcatg ggggtcgacc taattcttct taataaagtc aaagagtgtg   60

<210> SEQ ID NO 33
<211> LENGTH: 30
<212> TYPE: DNA
<213> ORGANISM: Artificial
<220> FEATURE:
<223> OTHER INFORMATION: Primer

<400> SEQUENCE: 33
gcaaggaatg gtgcatgcaa ggagatggcg                                30

<210> SEQ ID NO 34
<211> LENGTH: 33
<212> TYPE: DNA
<213> ORGANISM: Artificial
<220> FEATURE:
<223> OTHER INFORMATION: Primer

<400> SEQUENCE: 34
agcagccaac tcagcttcct ttcgggcttt gtt                            33

<210> SEQ ID NO 35
<211> LENGTH: 33
<212> TYPE: DNA
<213> ORGANISM: Artificial
<220> FEATURE:
<223> OTHER INFORMATION: Primer

<400> SEQUENCE: 35
cctgtacttc tcaatccagg gaacatcggg cat                            33

<210> SEQ ID NO 36
<211> LENGTH: 33
<212> TYPE: DNA
<213> ORGANISM: Artificial
<220> FEATURE:
<223> OTHER INFORMATION: Primer

<400> SEQUENCE: 36
atgcccgatg ttccctggat tgagaagtac agg                            33

<210> SEQ ID NO 37
<211> LENGTH: 51
<212> TYPE: DNA
<213> ORGANISM: Artificial

-continued

```
<220> FEATURE:
<223> OTHER INFORMATION: Primer

<400> SEQUENCE: 37
gtaacgccag ggttttccca gtcacgacgt tgtaaaagga cggccagtgc c          51
```

DNA REPLICATION FACTORS

BACKGROUND OF THE INVENTION

1. Field of the Invention

The present invention relates to two DNA replication factors capable of enhancing DNA polymerase activity from *Pyrococcus*, and to a DNA polymerase reaction system utilizing such factors.

2. Background Art

DNA polymerase is an enzyme useful for DNA sequencing reaction, polymerase chain reaction (PCR), radioactive labeling of DNA, in vitro synthesis of a mutated gene, and the like. DNA polymerases currently known can be generally classified into six families based on their amino acid sequence homology. Among them, DNA polymerases usually used as reagents in gene manipulation experiments belong to Family A polymerases such as typical *E. coli* DNA pol I and thermophilic bacterium *Thermus aquaticus* DNA polymerase (i.e., Taq DNA polymerase), and Family B polymerases such as typical T4 phage DNA polymerase. Various DNA polymerases having different optimum temperatures have been discovered from bacteria as well as from animals and plants. However, many of them, derived from mesophilic organisms and thus having low thermostability, are not suitable, for example, for PCR comprising heat denaturation of template DNA at 94° C. or over.

Enzymes from thermophilic bacteria, such as Taq DNA polymerase, are commercially available as thermostable DNA polymerases. However, all of them lack 3'-5' proofreading exonuclease activity, resulting in higher error rates during polymerase reactions such as PCR, and hence are not suitable for PCR with high fidelity and the like. Further, type B enzymes that are thermostable and have 3'-5' proofreading exonuclease activity, are isolated from hyperthermophilic archaea such as *Pyrococcus* and *Thermococcus*, and are commercially available. However, they have low primer extension activity and so are not suitable for PCR for long-strand DNA.

Examples of PCR techniques developed so far include conventional PCR using commercially available thermostable Pol A or Pol B, and isothermal PCR using φ29 DNA polymerase having high strand-displacement activity. The region replicable by the conventional Pol A or Pol B enzymes is short, the maximum being about 10 kb. In addition, the synthesis rate is as low as 30 b/sec. On the other hand, when φ29 DNA polymerase is used, PCR can be conducted at ambient temperature, so no expensive apparatus for amplification reaction is required and the procedure is simple. However, the use of random primers causes replicated regions to be relatively short, so that it is difficult to synthesize or produce a long DNA strand. Further, it is difficult to amplify DNA directly from the blood, body fluid, etc., by using the above conventional enzymes. This is because any of those conventional enzymes exhibits a reduced activity of DNA synthesis at a high salt concentration, and hence desalting is required to lower the salt concentration in the reaction solution.

The present inventors, for the first time, discovered a DNA polymerase from *Pyrococcus horikoshii*, which is thermostable and has 3'-5' proofreading exonuclease activity, and the gene thereof (JP Patent No. 3015878). Moreover, we successfully improved the DNA polymerase activity dramatically by removing an intein sequence from a large subunit of the DNA polymerase (JP Patent Publication (Kokai) No. 2001-299348A). Further, this DNA polymerase has a unique property that its primer extension activity becomes higher as the primer length is longer. However, this DNA polymerase also exhibits a reduced activity at a high salt concentration, although its activity is high at a low salt concentration.

Under these circumstances, the object of the present invention is to construct a new DNA polymerase reaction system utilizing a DNA polymerase, which is highly thermostable, has 3'-5' exonuclease activity by which mistakes occurring in a newly extended DNA strand are corrected, and also exhibits a high primer extension activity, wherein the high DNA polymerase activity is exerted even at a high salt concentration. Thereby, a novel technology is provided wherein a long-strand DNA region having a length of several Mb can be quickly replicated even under a high salt concentration without pretreatment.

SUMMARY OF THE INVENTION

In order to solve the above-mentioned problems, the present inventors focused on the hyperthermophilic archaeon *Pyrococcus horikoshii*, which grows at a temperature from 90 to 100° C., and discovered, from its gene sequences, genes expected to encode a clamp and a clamp loader, which are replication factors interacting with DNA polymerase to enhance DNA polymerase activity. Further, the clamp and the clamp loader were produced using *E. coli* from the discovered genes, and then it was confirmed that these proteins are stable at an elevated temperature (85° C. or higher), and enhance a primer extension activity of the DNA polymerase even at a concentration of sodium chloride as high as 0.2 M, thus the present invention having been completed.

In summary, the present invention comprises:

(1) A method for synthesizing a DNA, in which a primer DNA is extended by a DNA polymerase to synthesize the DNA complementary to a template DNA using deoxynucleotide triphosphates as substrates, wherein the enzyme reaction system comprises the DNA polymerase from *Pyrococcus horikoshii* and the two protein complexes of the following a) and b):

a) a protein complex composed of three molecules of a subunit and having a clamp function, the subunit being a protein comprising the amino acid sequence of SEQ ID NO: 8 or an amino acid sequence having at least 90% identity with the amino acid sequence of SEQ ID NO: 8;

b) a protein complex composed of one molecule of a large subunit and four molecules of a small subunit and having a clamp loader function, wherein the large subunit is a protein comprising the amino acid sequence of SEQ ID NO: 10 or an amino acid sequence having at least 90% identity with the amino acid sequence of SEQ ID NO: 10, and wherein the small subunit is a protein comprising the amino acid sequence of SEQ ID NO: 14 or an amino acid sequence having at least 90% identity with the amino acid sequence of SEQ ID NO: 14.

(2) The method of the above (1), wherein said enzyme reaction system does not contain ATP.

(3) The method of the above (1) or (2), wherein said enzyme reaction system contains sodium chloride at a concentration of from 0 to 200 mM/L or >0 to 200 mM/L.

(4) A reagent kit for synthesizing a DNA, wherein the kit comprises a DNA polymerase from *Pyrococcus horikoshii* and the two protein complexes of the following a) and b):

a) a protein complex composed of three molecules of a subunit and having a clamp function, the subunit being a protein comprising the amino acid sequence of SEQ ID NO: 8 or an amino acid sequence having at least 90% identity with the amino acid sequence of SEQ ID NO: 8;

b) a protein complex composed of one molecule of a large subunit and four molecules of a small subunit and having a clamp loader function, wherein the large subunit is a protein comprising the amino acid sequence of SEQ ID NO: 10 or an amino acid sequence having at least 90% identity with the amino acid sequence of SEQ ID NO: 10, and wherein the small subunit is a protein comprising the amino acid sequence of SEQ ID NO: 14 or an amino acid sequence having at least 90% identity with the amino acid sequence of SEQ ID NO: 14.

(5) The reagent kit of the above (4), wherein the kit is used for PCR and optionally contains written instructions, primers and/or ancillary reagents used for PCR.

(6) A protein comprising the amino acid sequence of SEQ ID NO: 8, or an amino acid sequence having at least 90% identity with the amino acid sequence of SEQ ID NO: 8, wherein, when three molecules of the protein subunit form a protein complex, the complex has a clamp function.

(7) A protein comprising the amino acid sequence of SEQ ID NO: 10 or an amino acid sequence having at least 90% identity with the amino acid sequence of SEQ ID NO: 10, wherein, when one molecule of the protein subunit forms a protein complex with four molecules of a small subunit comprising the amino acid sequence of SEQ ID NO: 14 or an amino acid sequence having at least 90% identity with the amino acid sequence of SEQ ID NO: 14, the complex has a clamp loader function.

(8) A protein comprising the amino acid sequence of SEQ ID NO: 14 or an amino acid sequence having at least 90% identity with the amino acid sequence of SEQ ID NO: 14, wherein, when four molecules of the subunit form a protein complex with one molecules of a large subunit comprising the amino acid sequence of SEQ ID NO: 10 or an amino acid sequence having at least 90% identity with the amino acid sequence of SEQ ID NO: 10, the complex has a function as a clamp loader.

(9) A DNA encoding of the protein of any one of the above (6) to (8).

(10) A DNA of the following (i) or (ii):

(i) a DNA comprising the nucleotide sequence of SEQ ID NO: 7, SEQ ID NO: 9, or SEQ ID NO: 13;

(ii) a DNA hybridizing with a DNA comprising a nucleotide sequence complementary to the nucleotide sequence of SEQ ID NO: 7, SEQ ID NO: 9, or SEQ ID NO: 13 under stringent conditions.

(11) A recombinant vector comprising the DNA of the above (9) or (10).

(12) A host cell comprising the recombinant vector of the above (11) is introduced therein.

According to the present invention, two novel DNA replication factors derived from *Pyrococcus horikoshii*, that is, a clamp and a clamp loader, is provided. Thus, an enzyme reaction system with which a long DNA strand is efficiently and accurately replicated by a DNA polymerase under conditions of a high temperature and a high salt concentration can be constructed. This enzyme reaction system is particularly useful for Long-PCR and the like, and new approaches for gene sequence analysis using such an enzyme reaction system can be developed.

BRIEF DESCRIPTION OF THE DRAWINGS

FIG. 1 illustrates the gene sequence of the large subunit of the DNA polymerase D (SEQ ID NO: 1). Underlined is the intein sequence.

FIG. 2 illustrates the amino acid sequence of the large subunit of the DNA polymerase D (SEQ ID NO: 2). Underlined is the intein sequence.

FIG. 3 illustrates the gene sequence of the small subunit of the clamp loader (RFC) (SEQ ID NO: 11). Underlined is an intein sequence.

FIG. 4 illustrates the amino acid sequence of the small subunit of the clamp loader (RFC) (SEQ ID NO: 12). Underlined is an intein sequence.

DETAILED DESCRIPTION OF THE PREFERRED EMBODIMENTS

Figure 5:
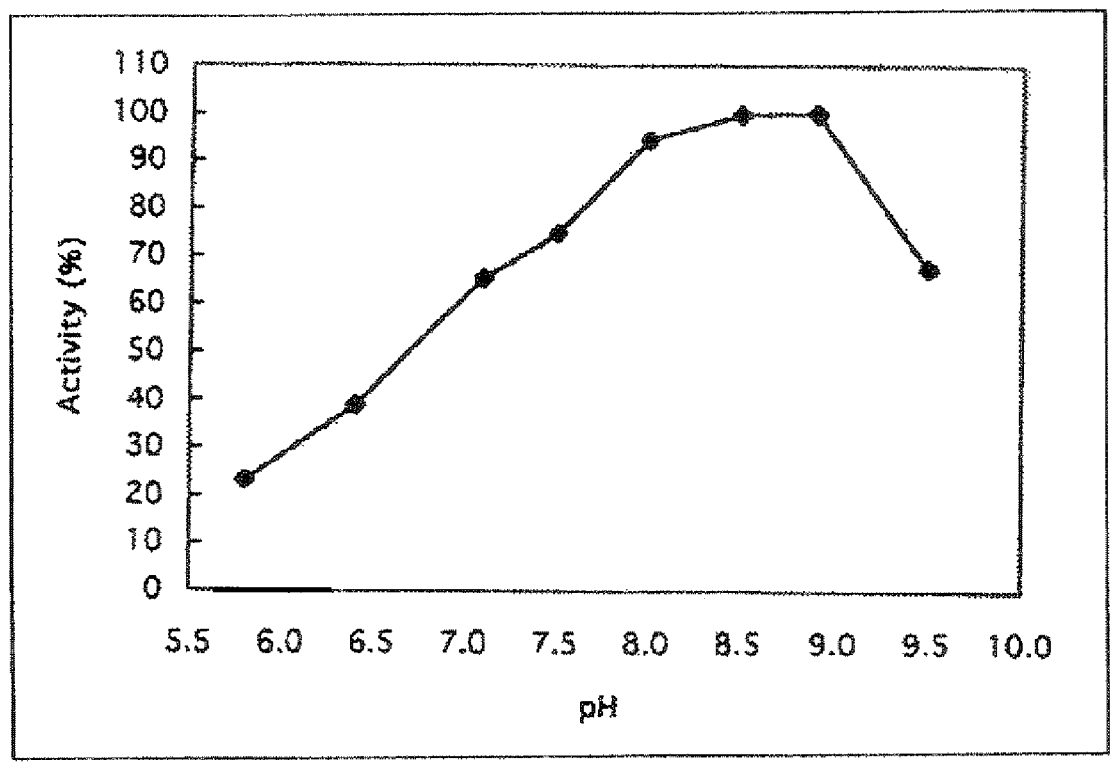
FIG. 5 illustrates the results determined for optimum pH of the DNA polymerase of the present invention.

Each of the DNA polymerase, the clamp (proliferating cell nuclear antigen, PCNA), and the clamp loader (replication factor, RFC) used in the present invention is a protein complex that is derived from *Pyrococcus* (JCM Accession Number 9974) and composed of multiple subunits.

The aforementioned DNA polymerase is a thermostable heterodimer enzyme composed of a small subunit and a large subunit without intein sequence, and has 3'-5' exonuclease activity and to DNA polymerase activity. This enzyme also has a primer extension activity dependent on primer length and has a property that the primer extension activity increases when the primer length is over 30 mer. A DNA polymerase composed of the small subunit and the large subunit without intein sequence is described in the previous patent application filed by the present inventors (JP Patent Application No. 2000-116257 (JP Patent Publication (Kokai) No. 2001-299348A)), and hence the enzyme without intein sequence itself is well known.

The invention of the previous application is based upon the fact that it was found for the first time that there is an intein sequence in the large subunit of the thermostable heterodimer enzyme, which is derived from *Pyrococcus horikoshii* and has DNA polymerase activity as well as 3'-5' exonuclease activity and that, when the intein sequence is removed, the primer extension activity of the enzyme is significantly improved. The amino acid sequence of the small subunit of this thermostable heterodimer enzyme from *Pyrococcus horikoshii* and the nucleotide sequence of the gene thereof are shown in SEQ ID NO: 6 and SEQ ID NO: 5, respectively. The amino acid sequence of the large subunit and the nucleotide sequence of the gene thereof are shown in SEQ ID NO: 2 and SEQ ID NO: 1 respectively, as well as in FIG. 2 and FIG. 1 respectively. The amino acid sequence of the intein portion corresponds to the region from amino acids 955 to 1120, and the nucleotide sequence thereof to the region from nucleotides 2863 to 3360 (the intein sequence is underlined in FIG. 2 and FIG. 1).

The amino acid sequence of the large subunit with no intein portion and the nucleotide sequence corresponding thereto are shown in SEQ ID NO: 4 and SEQ ID NO: 3, respectively. This enzyme is extremely thermostable and, even after treated at 85° C. for 1 hr., it retains 50% activity when compared to that before treatment. Additionally, after treated at 90° C. for 1 hr., it retains 20% activity. The optimum pH of the activity is pH 8.5.

The clamp (hereinafter, also referred to as PCNA) is a ring-shaped protein complex composed of plural subunits that tethers the DNA polymerase to a primed-template DNA during DNA replication. The clamp loader is a protein complex composed of plural subunits that opens and closes this clamp.

The clamp (PCNA) and the clamp loader (RFC), which are replication factors interacting with the DNA polymerase, a heterodimer, to enhance the DNA polymerase activity, can be obtained from the gene sequences of *Pyrococcus horikoshii* described above by the following procedures.

The gene of the clamp (PCNA) is amplified by PCR and extracted, which is then inserted into a vector such as a protein expression plasmid. The resulting plasmid is introduced into a host microorganism such as *E. coli*, which is then cultured to produce the clamp (PCNA). The produced clamp (PCNA) is heated and subsequently subjected to isolation and purification by column chromatography. Thus, the clamp (PCNA) is obtained. The purified PCNA has been revealed to be a homotrimer composed of the subunit having a molecular weight of 28 kDa. The amino acid sequence of the subunit and the nucleotide sequence corresponding thereto are shown in SEQ ID NO: 8 and SEQ ID NO: 7, respectively.

On the other hand, the clamp loader (RFC) from *Pyrococcus horikoshii* is composed of two subunits having different molecular weights. The subunit having a larger molecular weight has an intein sequence, and the amino acid sequence of this subunit and the nucleotide sequence corresponding thereto are shown in SEQ ID NO: 12 and SEQ ID NO: 11 respectively, as well as in FIG. 4 and FIG. 3 respectively (the intein sequences are underlined in FIG. 4 and FIG. 3). In the present invention, each of the regions upstream and downstream of the intein sequence in the DNA encoding the subunit (SEQ ID NO: 11; FIG. 3) is amplified by PCR, the resulting two DNA fragments are used as templates for amplification by Overlap PCR. Thus, the DNA encoding the subunit from which the intein sequence is removed is obtained. Hereinafter, the subunit without intein sequence is referred to as small subunit, and the subunit that originally contains no intein sequence is referred to as large subunit.

The DNA encoding the large subunit and the DNA encoding the small subunit without intein sequence, which subunits are of the clamp loader (RFC), are inserted into a single expression vector or two separate expression vectors. A host microorganism is then transfected with the resulting vector or vectors for coexpression. Further, the resulting proteins can be heat-treated and subsequently subjected to purification and isolation by column chromatography. Herein, the coexpression refers to the phenomenon wherein two DNAs are expressed in a host simultaneously and respective proteins corresponding to those DNAs are produced therein. The clamp loader having the activity recited in the present invention can be obtained by coexpression. The clamp loader thus obtained is composed of the large subunit having a molecular weight of 54 kDa and the small subunits containing no intein sequence and having a molecular weight of 38 kDa. The clamp loader is a heteropentamer, which is composed of one molecule of the large subunit and four molecules of the small subunit without intein sequence. The amino acid sequence of the 54 kDa large subunit and the corresponding nucleotide sequence are shown in SEQ ID NO: 10 and SEQ ID NO: 9, respectively. The amino acid sequence of the 38 kDa small subunit without intein sequence and the corresponding nucleotide sequence are shown in SEQ ID NO: 14 and SEQ ID NO: 13, respectively.

Each of the subunits composing the DNA polymerase, the clamp, or the clamp loader of the present invention includes a polypeptide comprising an amino acid sequence having at least 80 or 85%, preferably at least 90%, more preferably at least 95, 96, 97, or 98%, still more preferably at least 99% identity with the respective amino acid sequence of SEQ ID NO: 2, 4, or 6 (DNA polymerase subunit), SEQ ID NO: 8 (PCNA subunit), or SEQ ID NO: 10, 12, or 14 (RFC subunit). In particular, each of the subunits composing the above DNA polymerase, the clamp, and the clamp loader of the present invention is not limited to a polypeptide that comprises the amino acid sequence of each of SEQ ID NOS described above, but also includes a polypeptide that comprises an amino acid sequence in which one or more, preferably one or several, amino acids are deleted, substituted or added in any of these amino acid sequences, as long as the DNA polymerase activity, or the clamp function or clamp loader function, is still provided when it forms a respective protein complex as described above.

In the present invention, the term "several" refers to an integer of, for example, from 2 to 20, preferably from 2 to 15, more preferably from 2 to 10, from 2 to 9, from 2 to 8, from 2 to 7, from 2 to 6, from 2 to 5, from 2 to 4, or from 2 to 3.

Herein, in regard to amino acid substitution, amino acid side chains are different one another in terms of chemical properties such as hydrophobicity and electric charge or structural properties. Some highly conservative relationships, wherein the three-dimensional structure (also referred to as conformation) of the entire polypeptide is not essentially affected, are known from experience or actual physicochemical measurements. Substitution between amino acids in the present invention may be conservative substitution between amino acids which are similar to each other in terms of chemical or structural properties, or may be non-conservative substitution between amino acids which are different from each other in terms of such properties. Amino acids can be classified based on similarities in chemical and structural properties into the following groups.

In the hydrophobic amino acid groups, alanine (Ala), leucine (Leu), isoleucine (Ile), valine (Val), methionine (Met), and proline (Pro) are included.

In the polar amino acid group, serine (Ser), threonine (Thr), glycine (Gly), glutamine (Gln), asparagine (Asn), and cysteine (Cys) are included.

In the aromatic amino acid group, phenylalanine (Phe), tyrosine (Tyr), and tryptophan (Trp) are included.

In the acidic amino acid group, glutamic acid (Glu) and aspartic acid (Asp) are included.

In the basic amino acid group, lysine (Lys), arginine (Arg), and histidine (His) are included.

Examples of conservative substitution include the substitution between the following amino acids: glycine (Gly) and proline (Pro); glycine (Gly) and alanine (Ala) or valine (Val); leucine (Leu) and isoleucine (Ile); glutamic acid (Glu) and aspartic acid (Asp); glutamine (Gln) and asparagine (Asn); cystein (Cys) and threonine (Thr); threonine (Thr) and serine (Ser) or alanine (Ala); lysine (Lys) and arginine (Arg), etc.

Moreover, the DNA encoding each of the subunits composing the clamp or clamp loader of the present invention includes DNA comprising a nucleotide sequence having at least 80 or 85%, preferably at least 90%, more preferably 95, 96, 97, or 98%, still more preferably 99% identity with the respective nucleotide sequence of SEQ ID NO: 7 (PCNA subunit) or SEQ ID NO: 9, 11, or 13 (RFC subunit). In particular, the DNA encoding each of these subunits in the present invention is not limited to a DNA that comprises the nucleotide sequence of each of SEQ ID NOS described above, but also includes a DNA that encodes a protein comprising the amino acid sequence of each of SEQ ID NOS described above or a DNA that encodes a protein comprising an amino acid sequence in which one or more, preferably one or several, amino acids are deleted, substituted, or added in any of such amino acid sequences, wherein, when it forms each of the protein complexes described above, the DNA can encode a subunit capable of providing the respective functions.

The identity ranges and values for polynucleotide and polypeptide sequences herein include all intermediate subranges and values, for example, 80, 81, 82.5, 90, 92.5, 95, 95.1, 95.2, 95.3, 95.5, 99.65 or 99.75% identity to the corresponding sequence.

The DNA encoding each of the subunits composing the clamp or clamp loader of the present invention not only include DNA comprising the respective nucleotide sequence of SEQ ID NO: 7 (the PCNA subunit) or SEQ ID NO: 9, 11, or 13 (the RFC subunits) but also includes DNA comprising a mutated nucleotide sequence of any of these nucleotide sequences based on degeneracy of the genetic code. For example, the most suitable codon for a species different from *Pyrococcus horikoshii* can be selected based on the degeneracy of the genetic code for incorporation of the DNA into the cells of the species. Such a mutated nucleotide sequence refers to a nucleotide sequence comprising a different codon(s) for a certain amino acid(s).

Alternatively, the DNA encoding each of the subunits composing the clamp (PCNA) or clamp loader (RFC) of the present invention may include an analogue or homologue of the DNA comprising the nucleotide sequence of each SEQ ID NO described above, and is functionally equivalent thereto. As used herein, the term "functionally equivalent" means that the polypeptide encoded by the above analogue or homologue of the DNA has biological and/or biochemical functions that are equivalent to those of the peptide encoded by the DNA consisting of the nucleotide sequence of the respective SEQ ID NOS. More specifically, such a polypeptide has the function of each subunit composing the clamp (PCNA) or the clamp loader (RFC). Such a DNA includes a DNA that hybridizes with a DNA consisting of a nucleotide sequence complementary to the nucleotide sequence of any of SEQ ID NOS described above under stringent conditions. The stringent conditions refer to conditions under which specific hybrid is formed while non-specific hybrid not formed. The stringency comprises high or low stringency, and preferred is high stringent condition. In the low stringent condition, wash after hybridization is carried out, for example, using a solution of 5×SSC and 0.1% SDS at 42° C., and preferably using a solution of 5×SSC and 0.1% SDS at 50° C. In the high stringent condition, wash after hybridization is carried out, for example, using a solution of 0.1×SSC and 0.1% SDS at 65° C. Therefore, even when partial alterations of the full length nucleotide sequence of any SEQ ID NO described above can be generated by various artificial manipulations such as site-directed mutagenesis, random mutation using mutagens, or mutation, deletion or ligation of a DNA fragment cleaved by a restriction enzyme, the DNA variant which hybridizes with a DNA comprising a nucleotide sequence complementary to the nucleotide sequence of any of SEQ ID NOS described above under stringent conditions, and encodes a polypeptide having the function of each of the subunits composing the above clamp (PCNA) or the clamp loader (RFC) is included in the DNA encoding each subunit composing the clamp (PCNA) or the clamp loader (RFC) according to with the present invention, regardless of differences from the nucleotide sequences of SEQ ID NO: 7 (PCNA subunit) or SEQ ID NO: 9, 11, or 13 (RFC subunit).

Alternatively, the DNA encoding each of the subunits composing the clamp (PCNA) or the clamp loader (RFC) of the present invention may also include a DNA comprising a nucleotide sequence having at least 80%, preferably at least 90%, more preferably 95%, still more preferably 99% identity with the respective nucleotide sequence of SEQ ID NO: 7 (PCNA subunit) or SEQ ID NO: 9, 11, or 13 (RFC subunit).

The present invention also relates to a recombinant vector into which the DNA of the present invention has been incorporated. As used herein, the "recombinant vector" refers to a vector engineered to incorporate the DNA of the present invention into it by the recombinant DNA technology well known to person skilled in the art, including an expression vector. The "expression vector" refers to a DNA construct comprising the DNA of the present invention together with a nucleotide sequence(s) that can regulate the expression of the DNA of the present invention. "Regulatory sequences" are nucleotide sequences capable of regulating the expression of the DNA of the present invention, including, for example, a promoter, an enhancer, a polyadenylation signal, a replication initiation site, a ribosome-binding site or a Shine-Dalgarno sequence, a terminator, and the like. Preferred regulatory sequences are a sequence containing a promoter and a sequence containing a terminator. Preferably, such regulatory sequences are from the host organism.

Examples of vectors include a plasmid, a cosmid, a phage, a phagemid, BAC, YAC, a virus, and the like. The preferred vector is a plasmid.

The present invention further relates to a host cell comprising the above recombinant vector. Such a host cell is a transformed cell or a transformant, namely a host cell into which the above recombinant vector is introduced. Examples of host cells include cells derived from microorganisms such as bacteria and fungi, insect cells, and mammalian cells. The preferred host is a microorganism. Preferred microorganisms include *E. coli* and *Saccharomyces*.

The recombinant DNA technology employed in the present invention includes, for example, techniques as described in Sambrook, et al., Molecular Cloning: A Laboratory Manual, Cold Spring Harbor Laboratory Press, 1989; Ausubel, et al., Current Protocols in Molecular Biology, John Wiley & Sons, 1998, etc.

In the presence of PCNA and RFC, the primer extension activity of the heterodimer DNA polymerase is enhanced compared to that in the absence thereof. In particular, this effect is significant at a high salt concentration such as 200 mM NaCl. DNA, thereby, can be amplified without desalting directly from blood, body fluid, etc. Of course, DNA can also be synthesized from a sample containing no salt. Therefore, when the present invention is used in a practical application, no consideration is required for a salt concentration in a sample.

Further, when the RFC (the clamp loader) of the present invention loads the clamp on the DNA, adenosine triphosphate (ATP) is not required as an energy source. The enzyme reaction system of the present invention, in which the above heterodimer DNA polymerase coexists with PCNA and RFC, does not require the addition of adenosine triphosphate (ATP) as an energy source for loading the clamp on DNA in DNA synthesis. This is a further characteristic, because ATP inhibits the action of these DNA replication factors that enhance the DNA polymerase activity at a high salt concentration.

Any of the heterodimer DNA polymerase, PCNA and RFC of the present invention is thermostable, and the reagent kit for DNA synthesis comprising them in combination is suitable as a PCR reagent kit. Further, in the reagent kit, dATP, dTTP, dGTP and dCTP may be incorporated as substrates, and Family B DNA polymerase (Pol B) and the like may also be incorporated.

The reagent kit for synthesizing a DNA of the present invention comprises: a DNA polymerase from *Pyrococcus horikoshii* as well as (a) a protein complex composed of three molecules of a subunit and having a clamp function, wherein the subunit is a protein comprising the amino acid sequence of SEQ ID NO: 8 or an amino acid sequence having at least 90% identity with the amino acid sequence of SEQ ID NO: 8; and (b) a protein complex composed of one molecule of a large subunit and four molecules of a small subunit and having a clamp loader function, wherein the large subunit is a protein comprising the amino acid sequence of SEQ ID NO: 10 or an amino acid sequence having at least 90% identity with the amino acid sequence of SEQ ID NO: 10, and the small subunit being a protein comprising the amino acid sequence of SEQ ID NO: 14 or an amino acid sequence having at least 90% identity with the amino acid sequence of SEQ ID NO: 14. In the reagent kit of the present invention, each of the DNA polymerase, the protein complex (a), and the protein complex (b) may be contained in separate containers. In addition, in the reagent kit of the present invention, all of the DNA polymerase, the protein complex (a), and the protein complex (b) may be contained in the same container, or may be contained in any combination thereof.

Example 1

(1) The Culture of Archaeon

The archaeon JCM 9974 was cultured by the following procedure.

NaCl (13.5 g), $Na_2SO_4$ (4 g), KCl (0.7 g), $NaHCO_3$ (0.2 g), KBr (0.1 g), $H_3BO_3$ (30 mg), $MgCl_2.6H_2O$ (10 g), $CaCl_2$ (1.5 g), $SrCl_2$ (25 mg), 1.0 ml of a resazurin solution (0.2 g/L), yeast extract (1.0 g), and bacto peptone (5 g) were dissolved in water to give 1 L of a solution, pH was then adjusted to 6.8 followed by high-pressure sterilization. To the sterilized solution, then, the element sulfur sterilized by dry heat was added at the final concentration of 0.2%. The resulting medium was saturated with argon to render the medium anaerobic, into which JCM 9974 was then inoculated. When a solution of $Na_2S$ was added to the medium, the color of resazurin did not change into pink by $Na_2S$ in the medium, and thereby the anaerobic condition of the medium was confirmed. This medium was incubated at 95° C. for 2 to 4 days followed by centrifugation to collect the microorganisms.

(2) The Preparation of Chromosomal DNA

The chromosomal DNA of JCM 9974 was prepared by the following procedure. After the incubation was completed, the microorganism was collected by centrifugation at 5,000 rpm for 10 min. The collected microorganism was washed with a 10 mM Tris solution (pH 7.5) containing 1 mM EDTA twice, and then entrapped into a block of InCert Agarose (from FMC). This block was treated in a 1% N-lauroylsarcosine solution containing 1 mg/ml Protease K to separate and prepare the chromosomal DNA in the Agarose block.

(3) The Preparation of Clone Libraries Carrying the Chromosomal DNA

The chromosomal DNA obtained in the above (2) was subjected to partial digestion using the restriction enzyme HindIII followed by agarose gel electrophoresis to give a DNA fragment of about 40 kb in length. This DNA fragment was ligated, by using T4 ligase, with the Bac vector pBAC108L or the fosmid vector pFOS1 completely digested using the restriction enzyme HindIII. When the former vector was used, the DNA was introduced into *E. coli* immediately after the ligation by electroporation. When the latter vector pFOS1 was used, the DNA after the ligation was packaged into lambda phage particles in vitro using GIGA Pack Gold (from Stratagene), and *E. coli* was then infected with this packaged particles in order to introduce the DNA into the *E. coli*. The resulting *E. coli* population resistant to the antibiotic chloramphenicol was used as the BAC library or fosmid library. From these libraries, clones suitable for covering the chromosome of JCM 9974 were selected for clone alignment.

(4) The Nucleotide Sequencing for the BAC or Fosmid Clone

The nucleotide sequences were determined for the aligned BAC or fosmid clone by the following steps. The DNA of the BAC or fosmid clone collected from *E. coli* was sonicated to obtain DNA fragments, which were then subjected to agarose gel electrophoresis to give 1 kb or 2 kb DNA fragments. These DNA fragments were inserted into plasmid vector pUC118 at the HincII restriction enzyme site to prepare 500 shotgun clones per BAC or fosmid clone. The nucleotide sequence of each shotgun clone was determined by using an automatic DNA sequencer, Type 373 or Type 377 (PerkinElmer ABI). The nucleotide sequences obtained from the respective shotgun clones were assembled and edited by using an automatic DNA sequence assembly and analysis software, Sequencher, to determine the full-length nucleotide sequence for the BAC clone or the fosmid clone.

(5) The Identification of Genes Encoding DNA Polymerase, Clamp and Clamp Loader The nucleotide sequences of the BAC clone and the fosmid clone as determined above were analyzed by a large-scale computer, and the following genes were identified: the genes encoding the large subunit (underlined is an intein sequence in FIG. 1; SEQ ID NO: 1) and the small subunit (SEQ ID NO: 5) of the DNA polymerase; the gene encoding the clamp (PCNA) subunit (SEQ ID NO: 7); and the genes encoding the large subunit (SEQ ID NO: 9) and the small subunit (underlined is an intein sequence in FIG. 3; SEQ ID NO: 11) of the clamp loader (RFC).

Example 2

(1) The Construction of an Expression Plasmid for the Small Subunit of the DNA Polymerase D In order to form restriction enzyme (NdeI and BamHI) sites upstream and downstream of the region of the structural gene coding for the small subunit (SEQ ID NO: 5), DNA primers were synthesized. Using them, the restriction enzyme sites were inserted upstream and downstream of the gene by PCR.

```
Upper primer: PolS1;
                                        (SEQ ID NO: 15)
5'-TTTTGTCGACGTACATATGGATGAATTCGTAAAG-3'
(NdeI site is underlined)

Lower primer: PolS2;
                                        (SEQ ID NO: 16)
5'-TTTTGAGCTCTTTGGATCCTTAGAAGCTCCATCAGCA
CCACCT-3' (BamHI site is underlined)
```

After PCR, the extended strands were completely digested (at 37° C. for 2 hr) using the restriction enzymes (NdeI and BamHI), followed by purification of the structural gene. Further, pET11a or pET15b (Novagen) was cleaved using the restriction enzymes NdeI and BamHI and purified, which was then ligated with the above structural gene using T4 ligase at 16° C. for 2 hr. A part of the ligated DNA was introduced into competent E. Coli XL1-BlueMRF' cells to obtain colonies of transformants. From the resulting colonies, expression plasmids were purified by alkaline lysis. The resulting expression plasmid was abbreviated as pETIIa/PolS or pET15b/PolS, respectively. Absence of a random mutation on the structure gene was confirmed by DNA sequencing.

(2) The Construction of an Expression Plasmid for the Large Subunit of the DNA Polymerase D The gene coding for the large subunit was cloned into a pGEMEX-1 vector (from Promega) by a two-step procedure. The DNA fragment of upper part of said gene was obtained by PCR using the following two primers.

```
Upper primer: PolL1;
                                        (SEQ ID NO: 17)
5'-CTCGACTTTAGCATATGGCTCTGATGGAGC-3'
(NdeI site is underlined)

Lower primer: PolL2;
                                        (SEQ ID NO: 18)
5'-GCTTGTCGACGCCATAAACTTTGACATTATCCATTG
CGCGCTTAAGCAAC-3' (SalI site is underlined)
```

The PCR products were completely digested using NdeI and SalI, and then cloned into a pGEMEX-1 vector, abbreviated as pGEM/PolL1-2.

The DNA fragment of lower part of said gene was obtained by PCR using the following two primers.

```
Upper primer: PolL3;
                                        (SEQ ID NO: 19)
5'-TTTATGGCGTCGACAAGCTGAAGG-3'
(SalI site is underlined)

Lower primer: PolL4;
                                        (SEQ ID NO: 20)
5'-TATAACTTATGCATTGTGGTTATTTCGCTGAGAAG-3'
(NsiI site is underlined)
```

The PCR products were completely digested using SalI and NsiI and then cloned into the previously prepared pGEM/PolL1-2 to obtain pGEM/PolL carrying the full-length gene coding for the large subunit.

(3) The Construction of an Expression Plasmid for the Large Subunit without Intein As shown in FIG. 1, the gene coding for the large subunit of the DNA polymerase D from P. horikoshii contains one intein (coding for a proteinous intron). Therefore, the DNA fragment upstream of the intein was amplified by PCR using the primers PolL3 and PolL6, and the DNA fragment downstream of the intein was amplified by PCR using the primers PolL5 and PolL4. The DNA fragment without the intein was amplified by Overlap PCR using these two fragments and the primers PolL3 and PolL4. The products were then completely digested using the restriction enzymes SalI and NsiI, which were then cloned into the previously prepared pGEM/PolL1-2 to obtain pGEM/PolL(-Intein) carrying the gene coding for the large subunit without intein (SEQ ID NO: 3).

```
                                        (SEQ ID NO: 21)
PolL5: 5'-CACGCTGCAAAGAGGAGAAATTGCGATG-
       GTGATGAAGATGCT-3'

(SEQ ID NO: 22)
PolL6: 5'-AGCATCTTCATCACCATCGCAATTTCTC-
       CTCTTTGCAGCGTG-3'
```

(4) The Construction of a Plasmid Coexpressing the Small Subunit and the Large Subunit without Intein In order to produce the heterodimer DNA polymerase D of the present invention in a stable manner, a plasmid coexpressing the both subunits was constructed. First, in order to introduce a new multi-cloning site at the immediate upstream of the BamHI site of pET15b/PolS, PCR was performed using the primers PolSI and PolS3. Herein, as described below, the BamHI, NsiI, SalI, and SacII sites were coded in PolS3 from the 5'-terminal in this order. The resulting PCR products were treated with NdeI and BamHI, and then inserted into pET15b to construct pET15b/PolS(M) containing the multi-cloning site between the stop codon of the small subunit and the BamHI site.

Next, PCR was performed using the primers PolL7 and PolL2 with pGEM/PolL(-Intein) as a template. The resulting products contained a new SacII site at the 5'-terminal, and contained the portion from the ribosome-binding site to the SalI site in the coding region of the protein expression unit of pGEM/PolL(-Intein). This products were treated with Sac II and SalI, and then inserted into the multi-cloning site generated in pET15b/PolS(M). This plasmid was abbreviated as pET15b/PolSL1-2. On the other hand, pGEM/PolL(-Intein) was treated with SalI and NsiI to isolate the lower part of the gene of the large subunit (without the intein), which then was inserted into the protein expression unit of the pET15b/PolSL1-2 at the remaining SalI and NsiI sites thereof. The resulting plasmid was abbreviated as pET15b/PolSL(-Intein).

This expression plasmid, pET15b/PolSL(-Intein) enables the coexpression of the small subunit with a histidine tag attached at the N-terminal thereof and the large subunit without intein.

```
PolS3:
                                        (SEQ ID NO: 23)
5'-CG GGATCC ATGCAT G GTCGAC A CCGCGG
TCAGCACCACCTACT AAAGTCGAG-3' (BamHI, NsiI, SalI,
and SacII sites from 5'-terminal in this order are
underlined)

PolL7:
                                        (SEQ ID NO: 24)
5'-GGTGTCCGCGGCTCACTATAGGGAGACCAC-3' (SacII site
is underlined)
```

Example 3

The Construction of an Expression Plasmid for the Clamp (Pcna)

In order to introduce restriction enzyme (NdeI and XhoI) sites upstream and downstream of the region of the structural gene coding for PCNA (SEQ ID NO: 7), DNA primers were synthesized. Using them, the restriction enzyme sites were introduced upstream and downstream of the gene by PCR.

```
Upper primer: PCNA1;
                                        (SEQ ID NO: 25)
5'-GGGGGCATATGCCATTCGAAATAGTCTTTGAGGG-3'
(NdeI site is underlined)

Lower primer: PCNA2;
                                        (SEQ ID NO: 26)
5'-GGGGGCTCGAGTCACTCCTCAACCCTTGG-3' (XhoI
site is underlined.)
```

After PCR, the extended strands were completely digested (at 37° C. for 2 hr) using the restriction enzymes (NdeI and XhoI), followed by purification of the fragment of the structural gene. Further, pET11a', in which the XhoI site was added to the multi-cloning site of pET11a, was newly constructed, which was then cleaved using the restriction enzymes NdeI and XhoI and purified. The purified fragments were then ligated with the above structural gene using T4 ligase at 16° C. for 2 hr. A part of the ligated DNA was introduced into competent E. coli XL1-BlueMRF' cells to obtain colonies of transformants. From the resulting colonies, expression plasmids were purified by alkaline lysis. The resulting expression plasmid was abbreviated as pET11a'/PCNA. Absence of random mutation in the structure gene was confirmed by DNA sequencing.

Example 4

(1) The Construction of an Expression Plasmid for the Small Subunit of the Clamp Loader (RFC)

As shown in FIG. 3, the gene (RFCS) coding for one of the subunits composing the clamp loader derived from P. horikoshii contains one intein (coding for a proteinous intron; the underlined part in FIG. 3). Therefore, the DNA fragment upstream of the intein was amplified by PCR using the primers RFCS1 and RFCS3, and the DNA fragment downstream of the intein was amplified by PCR using the primers RFCS4 and RFCS2. The DNA fragment without the intein was amplified by Overlap PCR using these two fragments and the primers RFCS1 and RFCS2. Then, the products were completely digested using the restriction enzymes NdeI and BamHI followed by the purification of the structural gene (SEQ ID NO: 13). Further, pET11a (from Novagen) was cleaved using the restriction enzymes NdeI and BamHI followed by purification. The purified fragments were then ligated with the above fragment of the structural gene using T4 ligase at 16° C. for 2 hrs. Competent cells of E Coli XL1-BlueMRF' was introduced with an aliquot of the ligated DNA to obtain colonies of transformants. From the resulting colonies, expression plasmids were purified by alkaline lysis. The resulting expression plasmid was abbreviated as pET11a/RFCS.

```
RFCS1:
                                        (SEQ ID NO: 27)
5'-GGGGGGCATATGCATAATATGGAAGAGGTTCGCGAGG-3' (NdeI
site is underlined)

RFCS2:
                                        (SEQ ID NO: 28)
5'-GGGGGATCCTCACTTCTTCTTTCCAACTAAGGTAAA-3' (BamHI
site is underlined)

RFCS3:
                                        (SEQ ID NO: 29)
5'-GCAGGTCCTCCTGGTGTTGGAAAGACTACAGCAGCTTTAGCCCTC
TCA-3'

RFCS4:
                                        (SEQ ID NO: 30)
5'-TGAGAGGGCTAAAGCTGCTGTAGTCTTTCCAACACCAGGAGGAC
CTGC-3'
```

(2) The Construction of an Expression Plasmid for the Large Subunit of the Clamp Loader (RFC)

In order to introduce restriction enzyme (NdeI and BamHI) sites upstream and downstream of the region of the structural gene coding for the large subunit (SEQ ID NO: 9), DNA primers were synthesized. Therewith, the restriction enzyme sites were introduced upstream and downstream of the gene using PCR.

```
Upper primer: RFCL1;
                                  (SEQ ID NO: 31)
5'-GGGGGGCATATGCCGGATGTTCCATGGATTGAG-3'
(NdeI site is underlined)

Lower primer: RFCL2;
                                  (SEQ ID NO: 32)
5'-GGGGGATCCGGGGATGCATGGGGGTCGACCTAAT
TCTTCTTAATAAAGTCAAAGAGTGTG-3' (BamHI site is
underlined)
```

After PCR, the extended strands were completely digested (at 37° C. for 2 hr) using the restriction enzymes (NdeI and BamHI) followed by the purification of the fragment of the structural gene. Further, pET15b (from Novagen) was cleaved using the restriction enzymes NdeI and BamHI and purified. The purified fragments were then ligated with the above fragment of the structural gene using T4 ligase at 16° C. for 2 hr. A part of the ligated DNA was introduced into competent *E. coli* XL1-BlueMRF' cells to obtain colonies of transformants. From the resulting colonies, expression plasmids were purified by alkaline lysis. The resulting expression plasmid was abbreviated as pET15b/RFCL.

(3) The Construction of a System for Coexpressing the Large and Small Subunits of RFC In order to construct a system for coexpressing the large and small subunits of RFC by employing co-transformation, the gene coding for the large subunit (RFCL) was inserted between the NcoI site and the BamHI site of the multi-cloning site 2 of pACYCDuet-1 (Novagen) that is compatible (having an Ori sequence from a different origin) with a pET vector. The detailed procedure is explained below.

First, one NcoI recognition sequence in the RFCL gene was subjected to silent mutation using Overlap PCR. More specifically, using pET15b/RFCL as a template, the DNA fragment upstream of the NcoI recognition sequence was amplified by PCR using the primers RFCL3 and RFCL5, and the DNA fragment downstream of the NcoI recognition sequence was amplified by using the primers RFCL6 and RFCL4. The DNA fragment without the NcoI recognition sequence was amplified by Overlap PCR using these two fragments and the primers RFCL3 and RFCL4. The primers RFCL3 and RFCL4 have sequences that can anneal with the upstream and the downstream of the multi-cloning site of the pET15b vector, respectively, and hence the NcoI site and the BamHI site derived from the pET15b were contained in the Overlap PCR products. These products were completely digested using the restriction enzymes NcoI and BamHI followed by the purification of the fragment of the structural gene. On the other hand, pACYCDuet-1 was cleaved using the restriction enzymes NcoI and BamHI, followed by purification. The purified products were then ligated with the above fragment of the structural gene using T4 ligase at 16° C. for 2 hr. Competent cells of *E. Coli* XL2-Blue were introduced with a part of the ligated DNA to obtain colonies of transformants, which were resistant to chloramphenicol at the final concentration of 500 μg/ml.

From the resulting colonies, expression plasmids were purified by alkaline lysis. The resulting expression plasmid was abbreviated as pACYC/RFCL.

```
                                  (SEQ ID NO: 33)
RFCL3:  5'-GCAAGGAATGGTGCATGCAAGGAGATGGCG-3'

(SEQ ID NO: 34)
RFCL4:  5'-AGCAGCCAACTCAGCTTCCTTTCGGGCTTTGTT-3'

(SEQ ID NO: 35)
RFCL5:  5'-CCTGTACTTCTCAATCCAGGGAACATCGGGCAT-3'

(SEQ ID NO: 36)
RFCL6:  5'-ATGCCCGATGTTCCCTGGATTGAGAAGTACAGG-3'
```

Example 5

Expression of the Recombinant Genes

(1) The DNA Polymerase D

Competent *E. coli* cells (BL21-CodonPlus (DE-3)-RIL; from Stratagene) were thawed, 0.1 ml of which was transferred into a centrifuge tube. To the thawed cells, 0.005 ml of a solution of the expression plasmid was added and kept on ice for 30 min. Then, the cells were subjected to heat shock at 42° C. for 30 sec, to which 0.9 ml of SOC medium was then added followed by shaking at 37° C. for 1 hr. The cultured cells in an appropriate amount were plated onto a 2YT agar plate containing ampicillin, which was incubated at 37° C. overnight to obtain transformants.

The transformants were cultured in 2YT medium (2 L) containing ampicillin until the absorbance at 600 nm reached to 1, and then IPTG (isopropyl-β-D-thiogalactopyranoside) was added thereto and further cultured at 30° C. for 8 hr, followed by centrifugation (6,000 rpm for 20 min.) to collect the microorganisms.

(2) The Clamp (PCNA)

Competent *E. coli* cells (BL21-CodonPlus (DE-3)-RIL; from Stratagene) were thawed, 0.1 ml of which was transferred into a centrifuge tube. To the thawed cells, 0.005 ml of a solution of the expression plasmid was added and kept on ice for 30 min. Then, the cells were subjected to heat shock at 42° C. for 30 sec., to which then 0.9 ml of SOC medium was added followed by shaking at 37° C. for 1 hr. Subsequently, the cultured cells in an appropriate amount were plated onto a 2YT agar plate containing ampicillin, which was incubated at 37° C. overnight to obtain transformants. The transformant was named *E. coli* BL21(DE3) CodonPlus RIL/pET11a'/PCNA and deposited under the terms of the Budapest treaty with the International Patent Organism Depositary National Institute of Advanced Industrial Science and Technology (AIST Tsukuba Central 6, 1-1-1 Higashi, Tsukuba, Ibaraki, Japan) on Mar. 9, 2007, the assigned Accession Number being FERM BP-10796, which deposit was transferred from the national deposition under Accession Number FERM P-20911 (deposited on May 12, 2006).

The transformants were cultured in 2YT medium (2 L) containing ampicillin until the absorbance at 600 nm reached to 0.5, and then IPTG (at the final concentration of 0.5 mM) was added thereto and further cultured at 37° C. for 4 hr, followed by centrifugation (6,000 rpm for 20 min.) to collect the microorganisms.

(3) The Clamp Loader (RFC)

The large and small subunits of RFC were co-expressed by co-transformation using the two expression vectors. First, competent *E. coli* cells (BL21 (DE-3); from Stratagene) were thawed, 0.1 ml of which was transferred into a centrifuge tube. To the thawed cells, 0.005 ml of a solution of the expression plasmid pET11a/RFCS was added and kept on ice for 30 min. Then, the cells were subjected to heat shock at 42° C. for 30 sec, to which then 0.9 ml of SOC medium was added followed by shaking at 37° C. for 1 hr. Subsequently, the cultured cells in an appropriate amount were plated onto a 2YT agar plate containing ampicillin, which was incubated at 37° C. overnight to obtain transformants, *E. coli* BL21 (DE3)/pETIIa/RFCS. The transformants were further treated with $CaCl_2$ to prepare competent cells. To the resulting competent cells, 0.005 ml of a solution of the expression plasmid pACYC/RFCL was added and kept on ice for 30 min. Then, the cells were subjected to heat shock at 42° C. for 30 sec., to which then 0.9 ml of SOC medium was added followed by shaking at 37° C. for 1 hr. Subsequently, the cultured cells in an appropriate amount were plated onto a 2YT agar plate containing two antibiotics, ampicillin and chloramphenicol (at the final concentrations of 100 µg/ml and 50 µg/ml, respectively), which was incubated at 37° C. overnight to obtain the transformant *E. coli* BL21(DE3)/pET11a/RFCS/pACYC/RFCL. This transformant was deposited under the terms of the Budapest treaty with the International Patent Organism Depositary National Institute of Advanced Industrial Science and Technology (AIST Tsukuba Central 6, 1-1-1 Higashi, Tsukuba, Ibaraki, Japan) on Mar. 9, 2007, the assigned Accession Number being FERM BP-10797, which deposit was transferred from the national deposition under Accession Number FERM P-20912 (deposited on May 12, 2006).

The transformants were cultured in 2YT medium (200 ml) containing ampicillin and chloramphenicol until the absorbance at 600 nm reached to 0.6, and then IPTG (at the final concentration of 0.3 mM) was added thereto and further cultured at 25° C. for 20 hrs. followed by centrifugation (6,000 rpm for 20 min.) to collect the microorganisms.

Example 6

The Purification of Recombinant Proteins (1) The Thermostable DNA Polymerase D

The collected microorganisms were frozen at −20° C. and thawed, to which then twice the volume of 10 mM Tris HCl buffer (pH 8.0) and 1 mg of DNase to prepare suspension. The resulting suspension was incubated at 37° C. for 30 min., followed by sonication for 10 min. The suspension was further heated at 85° C. for 30 min. followed by centrifugation (11,000 rpm for 20 min.) to obtain the supernatant. This was used as a solution of the crude enzyme. Next, this solution of the crude enzyme was added to a Ni-column (from Novagen; a His-Bind metal chelation resin & His-Bind buffer kit were used) to carry out affinity chromatography. The 60 mM imidazole eluted fraction obtained thereby was transferred into 100 mM phosphate buffer (pH 6.0) using a Centriprep 30 (from Amicon). Further, this solution was adsorbed in a HiTrap SP column (from Pharmacia) and was then subjected to NaCl gradient elution. Next, SDS-PAGE was done for each fraction to determine a molecular weight of a protein contained therein. The subunits of the DNA polymerase of the present invention were expected to have a molecular weight of 144,000 Da and 70,000 Da, respectively. Hence, fractions having these molecular weights were collected, which were transferred into 50 mM Tris HCl buffer (pH 7.0) using a Centriprep 30 followed by further affinity chromatography using a HiTrap Heparin column (from Pharmacia) and NaCl gradient elution to obtain a purified enzyme.

(2) The Thermostable Clamp (PCNA)

The collected microorganisms were frozen at −20° C. and thawed, to which then twice the volume of 50 mM Tris HCl buffer (pH 8.0), 0.1 M NaCl, 2 mM 2-mercaptoethanol, 0.1 mM EDTA, and 10% glycerol to prepare suspension. The resulting suspension was subjected to sonication for 10 min. followed by centrifugation (30,000 g for 20 min.) to obtain the supernatant. This was further heated at 75° C. for 15 min. followed by centrifugation (30,000 g for 20 min.) to obtain the supernatant. This was still further heated at 80° C. for 10 min. followed by centrifugation to obtain the supernatant. Next, to the resulting supernatant, poly(ethyleneimine) (Sigma) and NaCl were added at the final concentrations of 0.15% and 0.58 M, respectively, which was then stirred at 4° C. for 30 min followed by centrifugation (30,000 g for 20 min.). To the supernatant, $(NH_4)_2SO_4$ was added until 80% saturation, which was then stirred on ice for 2 hrs. followed by centrifugation (30,000 g for 20 min) to recover the precipitate. This precipitate was dissolved in 50 mM Tris HCl buffer (pH 8.0), 0.1 M NaCl, 2 mM 2-mercaptoethanol, 0.1 mM EDTA, and 10% glycerol. This solution was dialyzed with the same buffer and added to an anion exchange column, HiTrap Q (from Amersham Pharmacia; 5 ml), which had been equilibrated with 50 mM Tris HCl buffer (pH 8.0), followed by from 0 to 1 M NaCl gradient elution in the same buffer. Further, the resulting solution was added to a Superdex 200 column (10/300; Amersham Pharmacia), which had been equilibrated with 50 mM Tris HCl buffer (pH 8.0) and 0.2 M NaCl, followed by elution with the same buffer to obtain purified PCNA.

(3) The Thermostable Clamp Loader (RFC)

The collected microorganisms were frozen at −20° C. and thawed, to which then twice the volume of 50 mM Tris HCl buffer (pH 8.0) containing a protease inhibitor (Complete, EDTA-free; from Roche) was added to prepare a suspension. The resulting suspension was homogenized using a French press, and then heated at 75° C. for 15 min. followed by centrifugation (30,000 g for 20 min) to obtain the supernatant. This supernatant was added to a HiTrap heparin column (from Amersham Pharmacia; 5 ml), which had been equilibrated with 50 mM Tris HCl buffer (pH 8.0), followed by from 0 to 1 M NaCl gradient elution in the same buffer. The eluted fractions were analyzed by SDS-polyacrylamide gel electrophoresis (SDS-PAGE) to identify the elution peak of the RFC complex composed of the large and small subunits. Further, the fractions having these elution peaks were collected and added to a Ni-column (from Novagen; a His-Bind metal chelation resin & His-Bind buffer kit were used) to carry out affinity chromatography. The 200 mM imidazole eluted fraction obtained thereby was concentrated using a Centriprep 30 (Amicon). This concentrated product was added to a Superdex 200 column (10/300; Amersham Pharmacia), which had been equilibrated with 50 mM Tris HCl buffer (pH 8.0) and 0.2 M NaCl, followed by elution with the same buffer to obtain the purified RFC complex.

Example 7

The Evaluations of the Reaction System of the DNA Polymerase (1) The Test Conditions (a) PCR In order to detect the activity of the DNA polymerase D of the present invention, PCR was performed using the aforementioned two DNA oligomers (Upper primer and Lower primer), and the expression vector pET15b/PolS encoding the small subunit of the DNA polymerase of the present invention as a template DNA. One cycle was composed of three steps (94° C. for 1 min.; 61° C. for 2 min.; 70° C. for 3 min.), and 35 cycles were repeated. The reaction solution (100 µl) contained 20 mM Tris HCl buffer (pH 8.8), 10 mM KCl, 4 mM MgSO$_4$, 0.1% Triton X-100, 0.375 mM dNTP mix, 100 pmol Upper primer, 100 pmol Lower primer, and 0.1 µg of the DNA polymerase.

(b) DNA Synthesis

DNA synthesis was based on the method by Kornberg, et al. (J. Biol. Chem., 237, 519-525; J. Biol. Chem., 236, 1487-1493). The reaction solution (200 µl) contained 20 mM Tris HCl buffer (H 8.8), 10 mM KCl, 10 mM (NH$_4$)$_2$SO$_4$, 2 mM MgSO$_4$, 0.1% Triton X-100, 0.25 mM dNTP mix, 0.37 Mbq ($\alpha$-$^{32}$P) dATP, 20 µg of salmon testicular DNA treated by heating and chilling, and 0.1 µg of the DNA polymerase. The reaction was performed at 75° C. for 30 min. After the reaction was completed, to the reaction solution, 0.5 mg of the salmon testicular DNA chilled on ice was added, and thereto 500 µl of 1 N perchloric acid and 500 µl of water, both chilled on ice, were added followed by centrifugation (9,000×g for 5 min.) to obtain an acid-insoluble fraction. This precipitate was dissolved in 300 µl of 0.2 N NaOH, and further thereto 300 µl of 1 N perchloric acid and 300 µl of water, both chilled on ice, were added followed by centrifugation to obtain an acid-insoluble fraction. This precipitate was washed with 1 ml of 1 N acetic acid followed by centrifugation. The resulting precipitate was dissolved in 0.4 ml of 2 N ammonia solution. The radioactivity was determined by the Cherenkov effect using a liquid scintillation counter. Herein, the amount of the enzyme that can incorporate 10 nmol of dNTPs in DNA synthesis at 75° C. for 30 min. is defined as 1 Unit.

(c) The Optimum pH

The optimum pH was determined by incorporation of radioactivity into the acid-insoluble fraction, wherein the reaction temperature was held at 75° C. under the above test conditions and pH was changed from 5.8 to 9.5 with a phosphate buffer in the acidic range and with a Tris HCl buffer in the basic range.

(d) The Optimum Concentration of Mg$^{2+}$

The optimum concentration of Mg$^{2+}$ was determined by the incorporation of radioactivity into the acid-insoluble fraction, wherein the reaction temperature was fixed at 75° C. under the above test condition and the concentration of MgSO$_4$ was changed from 0 mM to 20 mM.

(e) Thermostability

The enzyme solution (100 µl) for heating contained 20 mM Tris HCl buffer (pH 8.0 at 25° C.), 500 mM NaCl, 10 mM MgSO$_4$, and the enzyme of the present invention at a concentration of 0.1 mg/ml. This solution was heated for 1 hr. in the range of from 60° C. to 95° C. using a GeneAmp PCR System 2400 (PerkinElmer), and then, with the resulting solution, DNA synthesis was performed and the residual activity was determined by the incorporation of radioactivity into the acid-insoluble fraction.

(f) The Primer Extension Activity

The primer extension activity was determined by the following procedure. A single-strand DNA of M13 phage (0.2 µg) and each of the primers (0.5 pmol) (15 mer, 34 mer, and 50 mer), which had been 5'-labeled with $^{32}$P, were annealed in 20 mM Tris HCl buffer (pH 8.5), 0.05 Units of the DNA polymerase was added to the DNA mixture in the presence of 10 mM MgCl$_2$, and then the reaction was allowed to proceed at 75° C. The reaction was terminated after 2 min or 10 min by adding the Stop solution thereto. The reaction products were analyzed by electrophoresis with 15% polyacrylamide gel (PAGE) containing 8 M urea.

(g) The 3'-5' Exonuclease Activity

By using the 50 mer primer 5'-labeled with $^{32}$P (0.5 pmol), the 3'-5' exonuclease activity was determined. The reaction solution (20 µl) contained 20 mM Tris HCl buffer (pH 8.5), 12 mM MgCl$_2$, and 4 ng of the labeled DNA, to which 0.05 Units of the polymerase was added, and the reaction was allowed to proceed at 75° C. The reaction was terminated after 30 min. by adding the Stop solution thereto. The reaction products were analyzed by electrophoresis with 15% polyacrylamide gel (PAGE) containing 8 M urea.

(h) The Interaction Between RFC Complex and PCNA

The binding property of RFC complex and PCNA was examined by the following procedure. In 100 µl of the reaction solution (containing 10 mM MgCl$_2$, 0.5 M NaCl, and ATP at a predetermined concentration), 400 pmol of PCNA and 400 pmol of RFC complex were admixed and kept at room temperature for 20 min. Thereto, 40 µl of Ni$^{2+}$-chilating resin was added and stirred by shaking at room temperature for 10 min, followed by centrifugation at 5,000 g for 30 sec to recover the resin as the precipitate. This recovered resin was washed with 200 µl of 20 mM Tris HCl buffer (pH 8.0) containing 0.5 M NaCl, 10 mM MgCl$_2$, and 5 mM imidazole four times followed by elution of the target protein complex using 40 µl of 20 mM Tris HCl buffer (pH 8.0) containing 0.5 M NaCl, 10 mM MgCl$_2$, and 500 mM imidazole. The composition of the proteins in the eluted samples was analyzed by SDS-PAGE.

(i) The Effect of RFC Complex and PCNA on the DNA Polymerase Activity

The primed substrate, which would be a substrate of the DNA polymerase D, was prepared by the following procedure. First, the 5'-terminal of the 51 mer oligonucleotide (5'-GTAACGCCAGGGTTTTCCCAGTCAC-GACGTTGTAAAAGGACGGCCAGTGCC-3' (SEQ ID NO: 37)) was labeled with $^{32}$P. The reaction solution (20 µl) contained 1× kinase buffer (from Toyobo), 20 pmol of the above 51 mer oligonucleotide, 6 µl of γ-$^{32}$P ATP (3,000 Ci/mmol), and 2 µl of T4 Kinase. This reaction solution was allowed to react at 37° C. for 3 hrs. followed by heating at 95° C. for 3 min. The oligonucleotide labeled with $^{32}$P was purified using QIAquick Nucleotide Removal Kit (QIAGEN). Next, in 100 µl of 1×M buffer (from Toyobo), 2 nmol of M13 ssDNA and 4 pmol of the 51 mer oligonucleotide labeled with $^{32}$P were admixed and then boiled for 5 min. followed by allowing the solution to cool gradually for annealing.

Using the above primed M13 ssDNA as a template, DNA polymerase reaction was carried out. To the reaction system, RFC complex and PCNA were added, and thereby the effect of these DNA replication factors to enhance the DNA polymerase activity was evaluated. The composition and the final concentrations of the reaction solution (20 μl) were as follows:

20 mM Tris HCl buffer (pH 8.8)
10 mM KCl
10 mM $(NH_4)_2SO_4$
0.1% Triton X-100
6 mM $MgSO_4$
0.25 mM dNTPs
400 ng of the DNA polymerase
2 μg of PCNA
2 μg of the RFC complex
0.04 pmol of the $^{32}P$-labeled primed M13 ssDNA
50-200 mM NaCl
10 mM ATP This reaction solution (20 μl) was kept at 60° C. for 5 min. After the reaction was completed, 4 μl of the reaction termination solution (0.3 M NaOH, 60 mM EDTA, 0.1% Bromophenol Blue, and 10% glycerol) was added thereto. This solution was then boiled for 5 min. followed by analysis of molecular species in the reaction product by 1.2% alkaline agarose gel electrophoresis, with the electrode solutions of 50 mM NaOH and 1 mM EDTA.

(2) The Results of the Evaluations (a) The Properties of the DNA Polymerase D

1) The Protein Chemical Properties

The large subunit of the enzyme of the present invention was composed of 1,434 amino acid residues before the removal of the intein and 1,268 amino acid residues after the removal of the intein, and the respective molecular weights were 163,000 Da and 144,000 Da. The small subunit thereof was composed of 623 amino acid residues, the molecular weight being 70,000 Da.

2) The Improved Activity of the Active Enzyme by Coexpressing the Small Subunit and the Large Subunit without the Intein When expressed individually, each of the subunits was extremely unstable, and hence stable expression was not possible. Therefore, the coexpression system was constructed. Thereby, it was possible to express the active enzyme at a high level, and the physicochemical properties thereof and the mechanism of thermostability were able to be explored.

3) The Detection of DNA Synthesizing Activity and PCR

By using a solution of the crude enzyme from recombinant E. coli, the DNA synthesizing activity was examined. As shown in Table 1, no activity was detected with each of the subunits itself. The combination of the small subunit and the large subunit containing intein also exhibited no activity. From these results, it was evident that the heterodimer structure composed of the small subunit and the large subunit without intein is essential to exhibiting the activity. Further, the heterodimer enzyme pET15b/PolSL(-Intein) composed of the small subunit and the large subunit without intein was purified. This purified enzyme (0.1 μg) and 10 mM $MgSO_4$ were used to determine the activity to synthesize DNA. In the system with the enzyme, an increased radioactivity, 175 times or more, was detected when compared to that without the enzyme. Next, the purified enzyme of the present invention was used for PCR and it was confirmed that the amplified product had the same length as the target DNA fragment (1.9 kb) by agarose gel electrophoresis. On the other hand, in the system without the enzyme of the present invention, no PCR product was detected. From the above findings, it was further evident that the heterodimer DNA polymerase D of the present invention composed of the small subunit and the large subunit without intein has sufficiently activity.

TABLE 1

The detection of the DNA synthesizing activity using a solution of the crude enzyme (2 ml) obtained from the recombinant E. coli

| Enzyme source | Activity (CPM) |
| --- | --- |
| Negative control (distilled water only) | 2,567 |
| pET15b/PolS | 1,181 |
| pGEM/PolL | 4,777 |
| pGEM/PolL(-Intein) | 3,827 |
| pET15b/PolSL | 3,237 |
| pET15b/PolSL (-Intein) | 12,323 |
| Positive control (Deep Vent polymerase, 1 Unit) | 86,189 |

4) Optimum pH

The optimum pH at 75° C. was 8.5 (FIG. 5).

5) Optimum $Mg^{2+}$ Concentration

Figure 6:
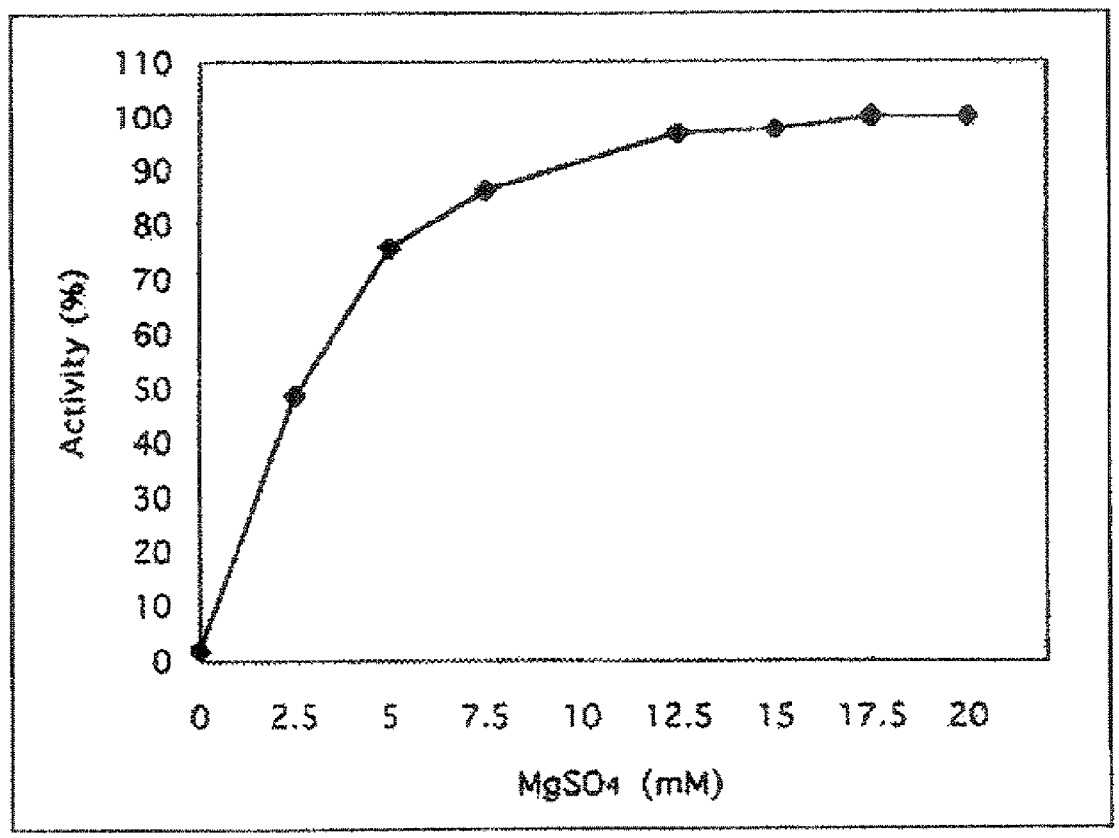
FIG. 6 illustrates the results determined for optimum $Mg^{2+}$ concentration of the DNA polymerase of the present invention.

The optimum $Mg^{2+}$ concentration of the enzyme of the present invention was 12 mM (FIG. 6).

6) Thermostability

Figure 7:
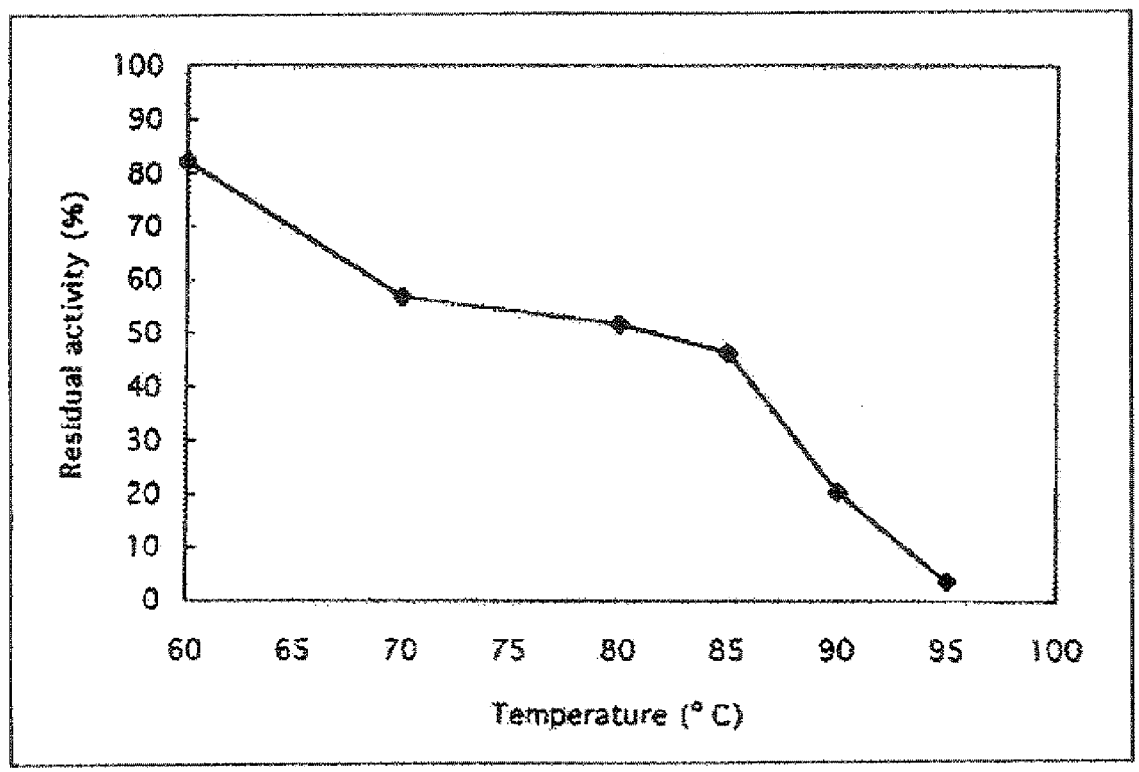
FIG. 7 illustrates the residual activity of the DNA polymerase of the present invention determined after heat treatment.

As shown in FIG. 7, the enzyme of the present invention retained 50% of the activity after heating at 85° C. for 1 hr. Further, it retained 20% of the activity even after heating at 90° C. for 1 hr.

7) Primer Extension Activity

Figure 8:
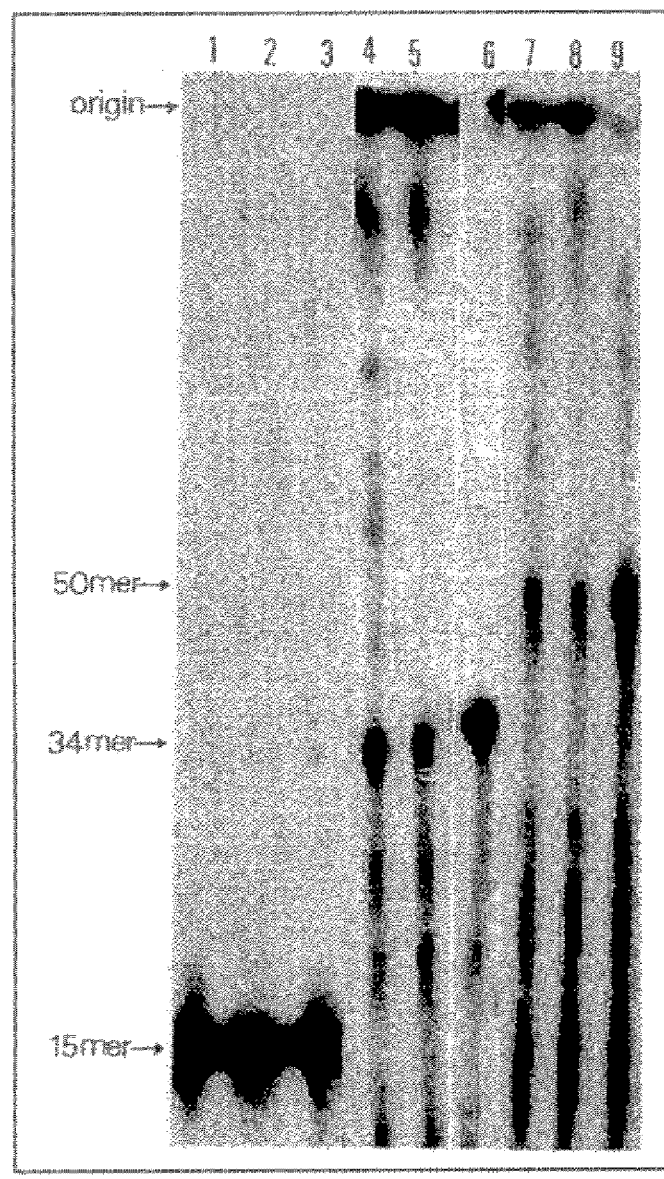
FIG. 8 illustrates the results tested for primer extension activity of the DNA polymerase of the present invention. For Lanes 1 to 3, Lanes 4 to 6, and Lanes 7 to 9, 15 mer primers, 34 mer primers, and a 50 mer primers were used, respectively. The reaction was constructed, for Lanes 1, 4, and 7, for 2 min in the presence of the enzyme; and for Lanes 2, 5, and 8, for 10 min in the presence of the enzyme. Lanes 3, 6, and 9 represent control experiments, in which no enzyme was added to the reaction system.

As shown in FIG. 8, while no primer extension activity was detected with the 15 mer primer by the enzyme of the present invention, when the primer was lengthened up to, for example, 34 mer or 50 mer long, the primer extension activity became greater. Such a primer extension activity dependent on primer length has not been reported with any other DNA polymerase.

8) 3'-5' Exonuclease Activity

Figure 9:
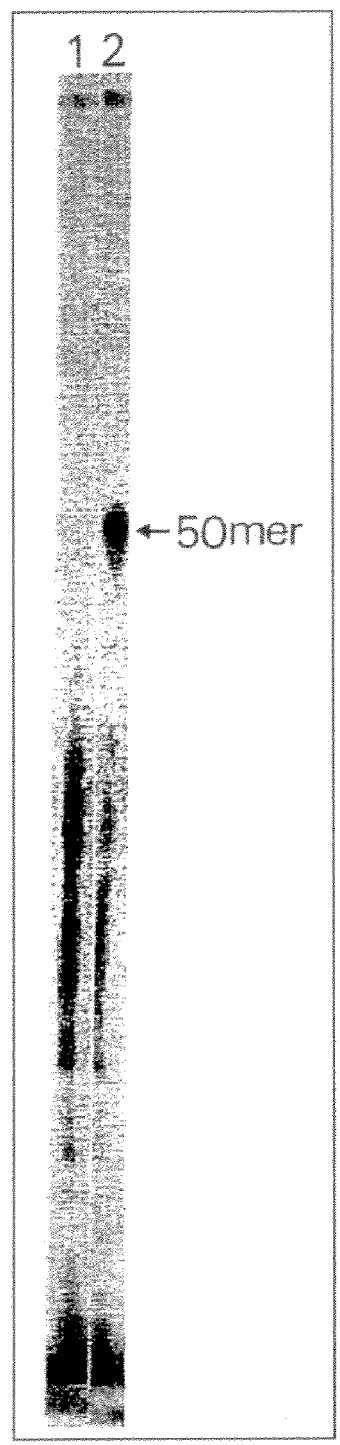
FIG. 9 illustrates the results tested for 3'-5' exonuclease activity of the DNA polymerase of the present invention. A 50 mer oligonucleotide was used as a substrate. For Lane 1, the reaction was conducted for 30 min in the presence of the enzyme, and Lane 2 represents a control with no enzyme.

As shown in FIG. 9, the enzyme of the present invention exhibited great 3'-5' exonuclease activity on the 50 mer oligonucleotide. From these findings, it was revealed that the enzyme of the present invention is a DNA-dependent DNA polymerase; is a heterodimer protein composed of two subunits having molecular weights of 144 kDa and 70 kDa, respectively; uses DNA as a template to synthesize a complementary strand; and has 3'-5' exonuclease activity.

(b) Properties of PCNA

Figure 10:
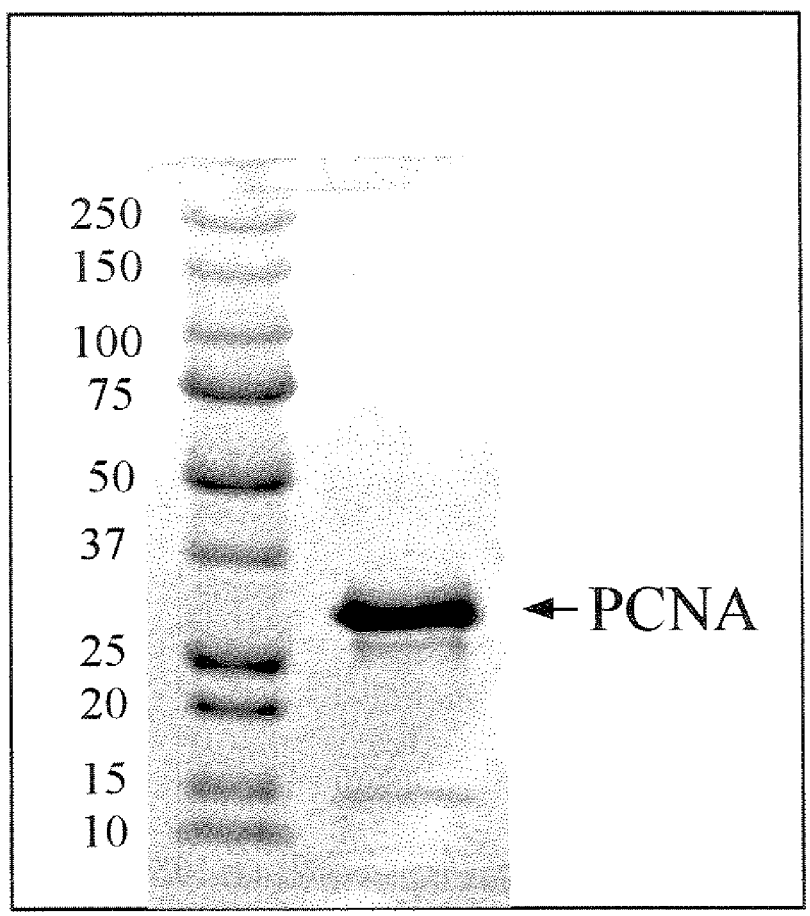
FIG. 10 illustrates the results determined by SDS-PAGE for the molecular weight of PCNA of the present invention. Lane 1 shows molecular markers, and Lane 2 shows purified PCNA.

PCNA was expressed in a large quantity in recombinant E. coli. Most of the proteins derived from the E. coli were removed by heating, the nucleic acids were removed with polyethyleneimine, and ammonium sulfate precipitation was carried out for concentration followed by anion exchange chromatography and gel filtration column chromatography for complete purification. As shown in FIG. 10, the apparent molecular weight of the PCNA subunit estimated by SDS-PAGE matched with the molecular weight of 28 kDa predicted from the gene. Further, the molecular weight of the native form thereof was predicted to be 110 kDa from the elution position in the gel filtration chromatography of the purified sample, and hence PCNA was revealed to be a homotrimer.

(c) Properties of RFC Complex

1) SDS-PAGE for RFC Complex

Figure 11:
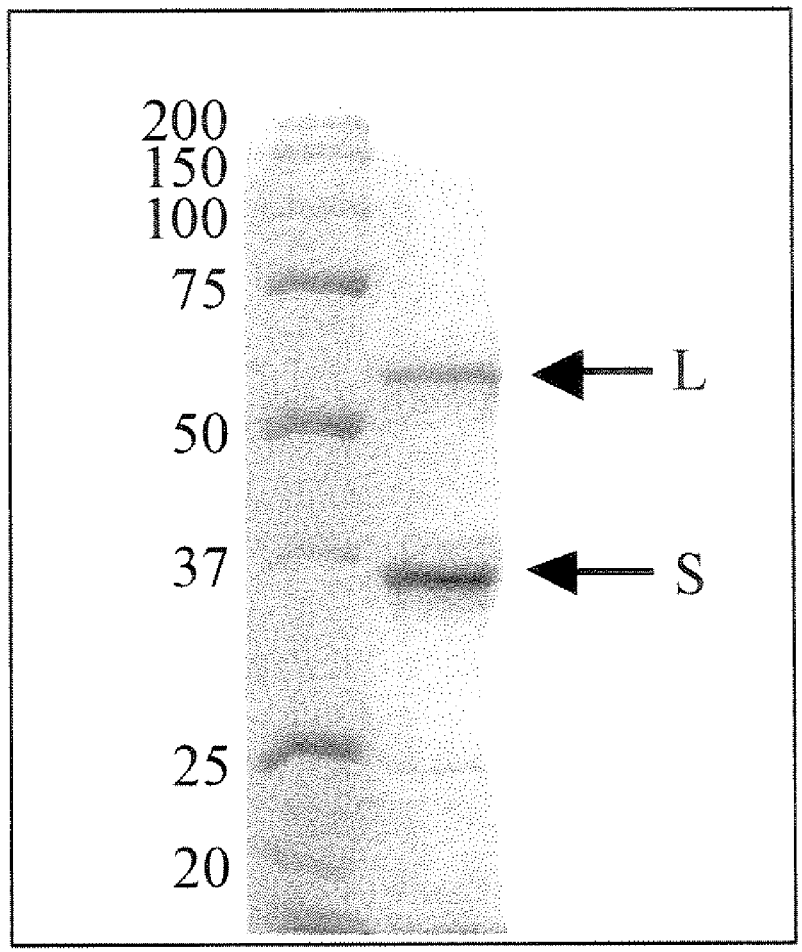
FIG. 11 illustrates the results determined by SDS-PAGE for the molecular weight of RFC complex of the present invention. Lane 1 shows molecular markers, and Lane 2 shows purified RFC complex, wherein L indicates the large subunit and S indicates the small subunit.

RFC complex was expressed in a large quantity in recombinant E. coli. Most of the proteins derived from the E. coli were removed by heating, and then affinity chromatography using heparin, affinity chromatography using nickel resin for the histidine tag present at the N-terminal of the large subunit, and gel filtration column chromatography were carried out for complete purification. As shown in FIG. 11, the apparent molecular weights of the large subunit (L) and the small subunit (S) of RFC complex estimated by SDS-PAGE were 60 kDa and 36 kDa, respectively, which approximately matched with the respective molecular weights of 54 kDa and 38 kDa predicted from the gene. Further, the molar ratio of the large subunit and the small subunit was 1:4, which was calculated from the dye-coupling intensities of the bands of the large and small subunit proteins, and hence the native form thereof was revealed to be a heteropentamer.

(d) Recognition of PCNA by RFC Complex in the Absence of ATP

Figure 12:
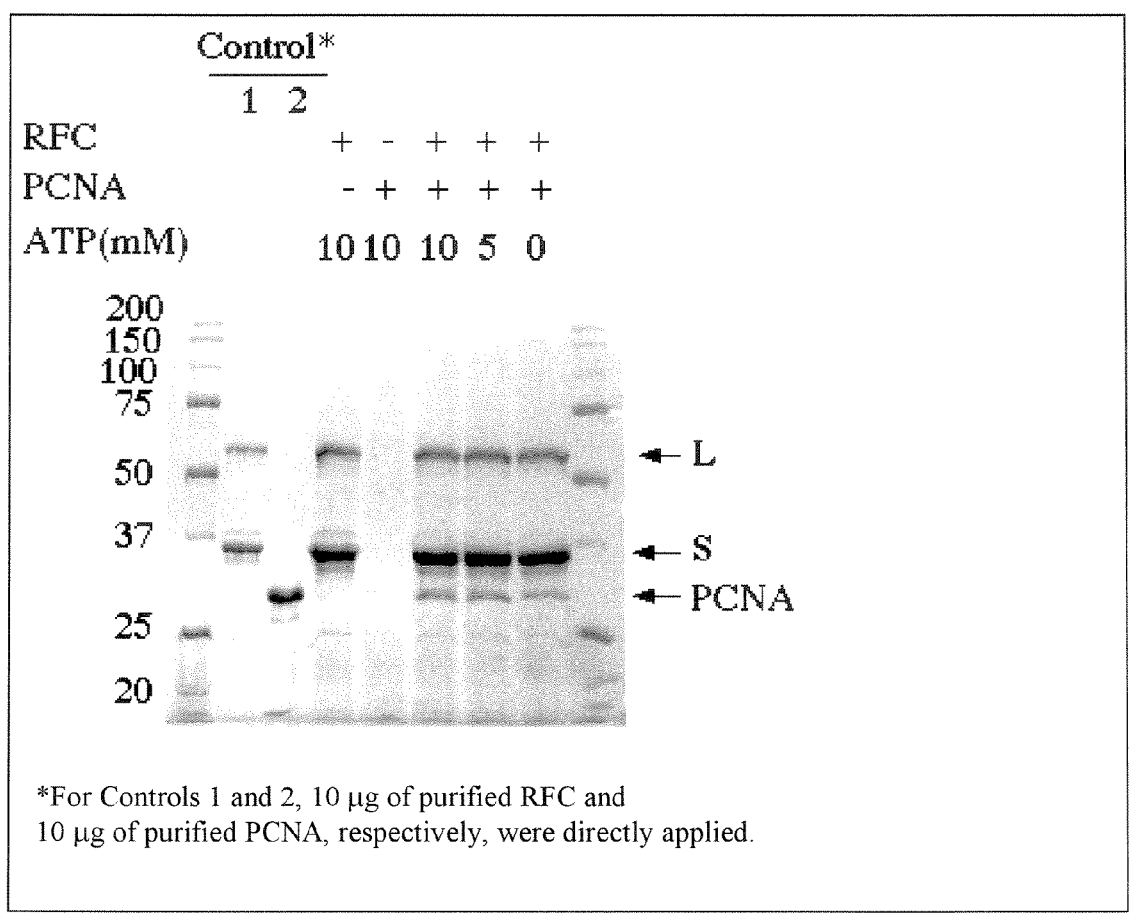
FIG. 12 illustrates the results of the pull-down assay of PCNA by RFC complex of the present invention. The interaction between RFC complex and PCNA was analyzed in the presence or absence of ATP by SDS-PAGE.

PCNA that bound to RFC complex was pulled down by using the histidine tag of RFC complex and nickel resin, which then was analyzed by SDS-PAGE. The results were shown in FIG. 12. From these results, it was revealed that both of RFC complex and PCNA were purified as active forms, and that RFC complex and PCNA recognize each other and have an activity to be bound together. Further, it was shown that this binding is not dependent on ATP.

Figure 13:
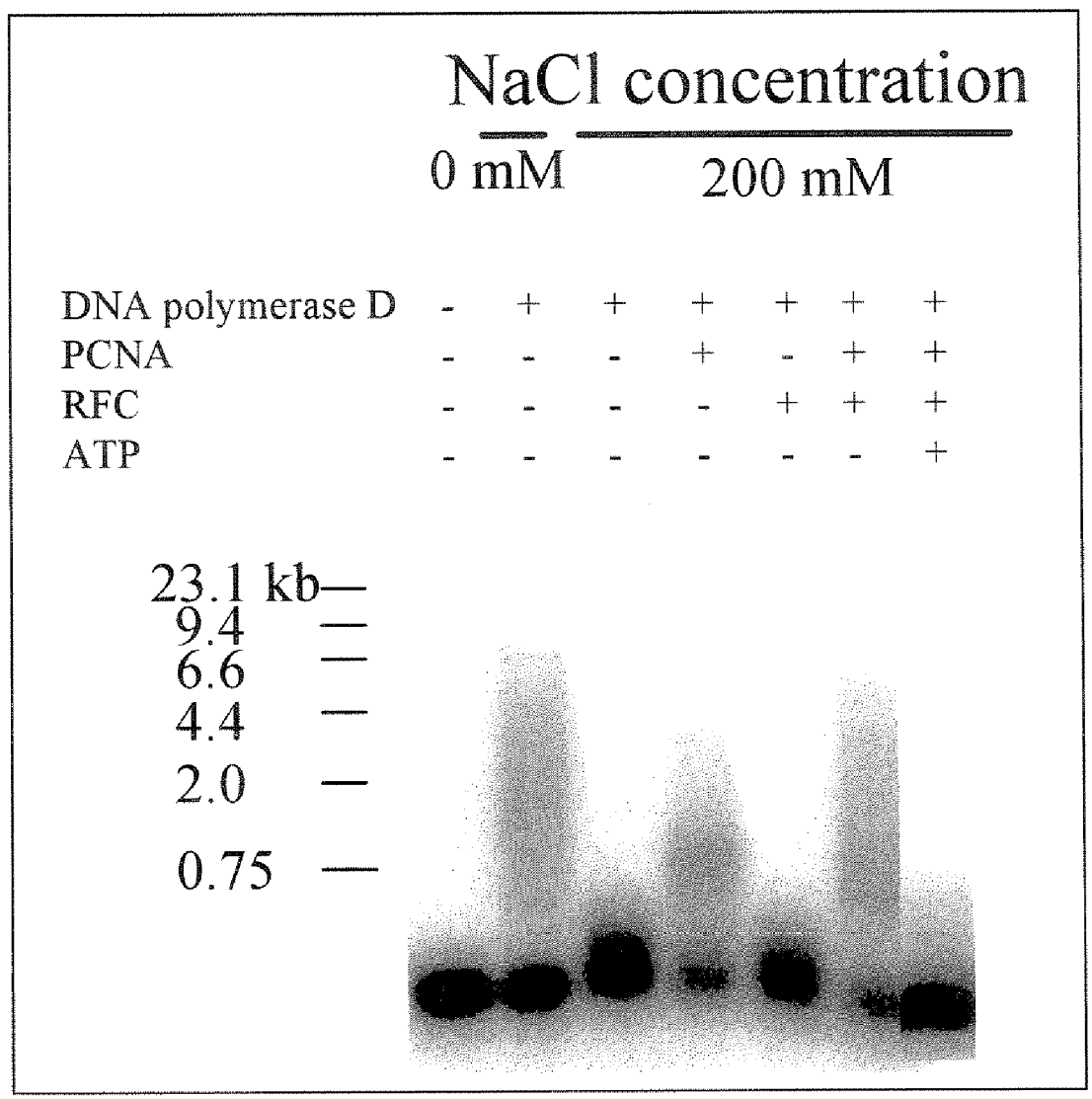
FIG. 13 illustrates the results tested for the effect of RFC complex and PCNA on enhancement of the activity of DNA polymerase D. ATP was used at the concentration of 10 mM.

(e) Requirement of ATPp for RFC Complex and PCNA to Enhance the Activity of the DNA Polymerase at a High Salt Concentration As shown in FIG. 13, it was revealed that while the DNA polymerase D by itself was not able to exhibit DNA polymerase activity in the presence of 200 mM NaCl, when PCNA was added thereto, the enzyme was able to synthesize DNA up to 0.75 kb. On the other hand, it was revealed that when RFC complex and PCNA were added to the DNA polymerase D in the presence of 200 mM NaCl, the enzyme was able to synthesize the full-length complementary strand of M13ssDNA (7.2 kb) at 60° C. for 5 min. At this time, the addition of ATP was not required. On the contrary, it was found that, when 10 mM ATP was present, the effect of RFC complex and PCNA to enhance the DNA polymerase activity at a high salt concentration was significantly inhibited.

From the above results, it was revealed that the primer extension activity of the heterodimer DNA polymerase of the present invention at a high salt concentration can be significantly enhanced in the presence of PCNA and RFC, when compared to that in the absence thereof.

What is claimed is:

1. A method for synthesizing deoxyribonucleic acid (DNA) comprising:
   synthesizing a complement of a template DNA by contacting the template DNA with a primer and a DNA polymerase in the presence of deoxynucleotide triphosphates within an enzyme reaction system;
   wherein said enzyme reaction system comprises a DNA polymerase from *Pyrococcus horikoshii*, protein complex (a), and protein complex (b), where
   (a) is a protein complex having a clamp function composed of three molecules of a subunit comprising SEQ ID NO: 8, and
   (b) is a protein complex having a clamp loader function composed of one molecule of a large subunit comprising SEQ ID NO: 10 and four molecules of a small subunit comprising SEQ ID NO: 14.

2. The method according to claim 1, wherein the enzyme reaction system does not contain ATP.

3. The method according to claim 1, wherein the enzyme reaction system contains sodium chloride at a concentration ranging from 0 to 200 mM.

4. The method according to claim 1, which is performed at a pH ranging from 6.0 to 7.5.

5. The method according to claim 1, which is performed at a pH ranging from 7.5 to 9.5.

6. The method according to claim 1, which is performed at a $Mg^{2+}$ concentration ranging from 2.5 to 12.5 mM.

7. The method according to claim 1, which is performed at a $Mg^{2+}$ concentration ranging from 12.5 to 20 mM.

8. The method according to claim 1, which is performed at a temperature ranging from 60 to 70° C.

9. The method according to claim 1, which is performed at a temperature ranging from 70 to 85° C.

10. The method according to claim 1, which is performed at a temperature ranging from 85 to 95° C.

* * * * *